(12) United States Patent
Ko et al.

(10) Patent No.: US 11,794,000 B2
(45) Date of Patent: Oct. 24, 2023

(54) ELECTRICAL MUSCLE STIMULATION ELECTRODE MASK PAD AND METHOD USING THE SAME

(71) Applicant: LUTRONIC CORPORATION, Goyang (KR)

(72) Inventors: Kwang Chon Ko, Paju (KR); James Bartholomeusz, Beverly Hills, CA (US)

(73) Assignee: LUTRONIC CORPORATION, Goyang (KR)

(*) Notice: Subject to any disclaimer, the term of this patent is extended or adjusted under 35 U.S.C. 154(b) by 269 days.

(21) Appl. No.: 17/129,216

(22) Filed: Dec. 21, 2020

(65) Prior Publication Data

US 2022/0001168 A1 Jan. 6, 2022

(30) Foreign Application Priority Data

Jul. 2, 2020 (KR) .................. 10-2020-0081453

(51) Int. Cl.
*A61N 1/36* (2006.01)
*A61N 1/04* (2006.01)
*A61N 1/06* (2006.01)

(52) U.S. Cl.
CPC ......... *A61N 1/0492* (2013.01); *A61N 1/0452* (2013.01); *A61N 1/0476* (2013.01); *A61N 1/06* (2013.01); *A61N 1/36003* (2013.01); *A61N 1/3603* (2017.08); *A61N 1/36034* (2017.08)

(58) Field of Classification Search
CPC .............. A61N 1/0492; A61N 1/36034; A61N 1/3603; A61N 1/0452; A61N 1/0476; A61N 1/06; A61N 1/36003; A61N 1/36031; A61B 5/053

See application file for complete search history.

(56) References Cited

U.S. PATENT DOCUMENTS

| | | |
|---|---|---|
| 2009/0079550 A1* | 3/2009 | Makinen .............. G09B 21/003 340/407.2 |
| 2009/0319003 A1 | 12/2009 | Castel |
| 2011/0106226 A1* | 5/2011 | Szasz ................... A61N 1/0404 607/101 |
| 2012/0203156 A1 | 8/2012 | Dar |
| 2012/0283800 A1 | 11/2012 | Perryman |

(Continued)

FOREIGN PATENT DOCUMENTS

| | | |
|---|---|---|
| JP | 2000-93526 A | 4/2000 |
| JP | 2003-250913 A | 9/2003 |

(Continued)

*Primary Examiner* — Ankit D Tejani
*Assistant Examiner* — Joshua Brendon Solomon

(57) ABSTRACT

The present disclosure relates to an EMS electrode pad. Each electrode may be provided to correspond to the shape and size of the divided area according to the virtual line. The EMS electrode pad and the EMS method using the same according to the present invention may minimize the edge current effect by the shape of the electrode to which electric energy is applied. In addition, energy transfer efficiency may be improved by capacitive coupling between the electrode and the skin. In addition, due to the coating of the electrode, a rate of contact with an affected part may be increased so that current may be applied evenly to each part.

19 Claims, 30 Drawing Sheets

(56) References Cited

U.S. PATENT DOCUMENTS

| | | | |
|---|---|---|---|
| 2012/0330394 A1* | 12/2012 | Dar | A61F 5/0102 |
| | | | 607/149 |
| 2014/0194949 A1* | 7/2014 | Wichner | A61N 1/323 |
| | | | 607/48 |
| 2014/0222102 A1* | 8/2014 | Lemus | A61N 1/36003 |
| | | | 607/48 |
| 2016/0147079 A1 | 5/2016 | Sharp et al. | |
| 2017/0209684 A1* | 7/2017 | Axelgaard | A61N 1/0492 |
| 2018/0296831 A1* | 10/2018 | Matsushita | A61N 1/3603 |
| 2019/0133673 A1* | 5/2019 | Boll | A61B 18/14 |
| 2019/0167988 A1 | 6/2019 | Shahriari | |
| 2020/0054285 A1* | 2/2020 | Lemons | A61N 1/0492 |

FOREIGN PATENT DOCUMENTS

| | | |
|---|---|---|
| KR | 10-2013-0136487 A | 12/2013 |
| KR | 1020170070232 A | 6/2017 |

* cited by examiner

FIG. 22
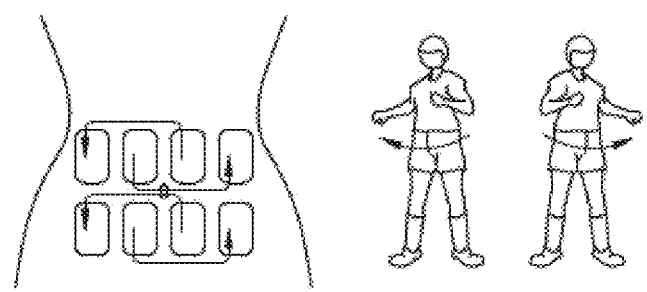
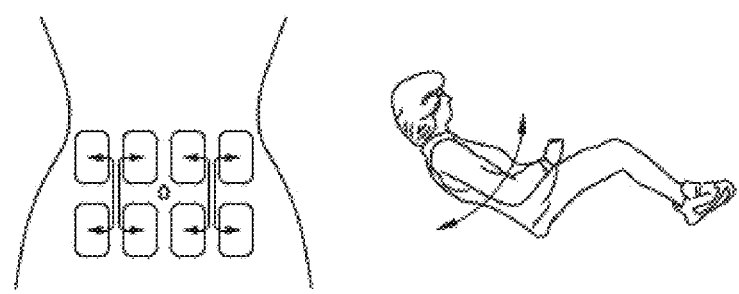
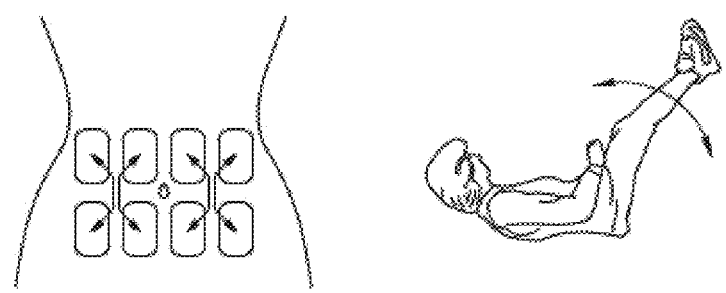

ELECTRICAL MUSCLE STIMULATION ELECTRODE MASK PAD AND METHOD USING THE SAME

CROSS-REFERENCE TO RELATED APPLICATIONS

Priority to Korean patent application number 10-2020-0081453 filed on Jul. 2, 2020 the entire disclosure of which is incorporated by reference herein, is claimed.

BACKGROUND OF THE DISCLOSURE

Field of the Disclosure

The present disclosure relates to an electrical muscle stimulation (EMS) electrode pad which includes a plurality of split electrodes and performs EMS, and an EMS mask pad comprising the EMS electrode pad and an EMS method using the same.

Related Art

Recently, the use of electrical muscle stimulation (EMS) that simulates nerves to contract and strengthen muscles using electrical energy is spreading. EMS may be used to maximize exercise effects and is known to help increase muscle mass and burn fat. In addition, EMS may be performed on muscles with paralysis symptoms due to nerve damage caused by a superficial wound so as to be used for a treatment through muscle strengthening.

In relation to an electrode pad used for such EMS, Korean Patent Laid-Open Publication No. 10-2017-0070232 discloses an electrode pad configured as a patch. However, such a related art pad does not apply a uniform current to an attached part and current is concentrated on an edge portion of a current applied portion due to an edge current effect. In addition, a skin is unintentionally heated when current is applied through the skin.

SUMMARY

The present disclosure provides an electrical muscle stimulation (EMS) electrode pad and an EMS method using the same, capable of solving the problem of the edge current and heating that occur in the related art EMS electrode.

In an aspect, an electrical muscle stimulation (EMS) electrode pad includes: a base having a plate-like shape; a plurality of electrodes arranged on a lower surface of the base; a plurality of first connection portions penetrating the base in a thickness direction and having one side electrically connected with each of the plurality of electrodes; and a second connection portion disposed on an upper surface of the base and connected with the other side of the plurality of first connection portions, wherein the plurality of electrodes are provided in virtual sections divided by a plurality of first virtual lines and a plurality of second virtual lines on the lower surface of the base, the first line forms a path directing toward an edge from a center portion of the lower surface of the base, and the second line is configured as a annular path based on which a center portion of the base is an inner side.

At least some of the plurality of first lines may be formed along a curved path.

At least some of the plurality of first lines may be formed along a path of a sinusoidal wave.

The first line may have a length smaller than a wavelength of the sinusoidal wave.

An interval between one second line and another second line adjacent thereto may increase so that a size of the section may increase in a direction toward the edge portion from the center portion, and at least some of the plurality of electrodes may be configured to increase in size in the direction toward the edge portion from the center portion.

The second line may be formed along a stadium-shape path.

The plurality of electrodes may each have a shape corresponding to a shape of a virtual region divided by the first line and the second line.

The plurality of electrodes may be insulated from each other on the lower surface of the base.

The plurality of electrodes may be spaced apart from each other by a predetermined distance on the lower surface of the base.

The electrode may be formed in a flat plate shape.

The EMS electrode pad may further include a shielding layer configured to cover the second connection portion and formed of an insulating material.

The EMS electrode pad may further include a connector configured to receive RF energy from the outside and electrically connected to one side of the second connection portion.

The base may be formed of a flexible material.

The base may be formed of a rigid material.

The EMS electrode pad may further include a dielectric layer covering the plurality of electrodes.

When a lower surface of the dielectric layer comes into contact with a skin, capacitive coupling may be formed between the plurality of electrodes in contact with an upper surface of the dielectric layer and the contacted skin.

The EMS electrode pad may be configured as a pair to receive bipolar RF energy.

The dielectric layer may be formed of ceramic or polytetrafluoroethylene (PTFE).

The EMS electrode pad may further include a conductive layer provided on a surface of the plurality of electrodes which comes into contact with the skin.

The conductive layer may be formed of graphene.

The conductive layer may be provided in each of the plurality of electrodes.

The conductive layer may be configured to cover the plurality of electrodes.

In another aspect, an electrical muscle stimulation (EMS) method includes: attaching an EMS electrode pad of an EMS device to a plurality of points of a tissue; performing impedance matching between the EMS device and the tissue in a state where the EMS electrode pad is attached; transferring RF energy to simulate muscle according to a preset sequence; and removing the EMS electrode pad from the tissue, wherein, in the transferring of RF energy, RF energy is applied to each of sections divided by a first virtual line in a sinusoidal wave form and a second virtual line having a stadium shape in a portion where each of the EMS electrodes is attached.

In the transferring of RF energy, RF energy may be applied through a larger area in a direction toward an outer side among portions where the EMS electrode is attached.

The transferring of RF energy may be performed by applying monopolar RF energy.

The transferring of RF energy may be performed by applying bipolar RF energy.

In the attaching of the EMS electrode, EMS electrodes configured as at least a pair may be attached, and the transferring of the RF energy may be performed by applying RF energy to the EMS electrodes configured as at least the pair.

The performing of impedance matching may be performed in a state of capacitive coupling is formed between the EMS electrode pad and the tissue.

The transferring of RF energy may be performed by applying RF energy through a graphene layer disposed between the plurality of electrodes and the tissue.

The transferring of RF energy may include a parameter adjusting operation of adjusting a parameter of RF energy according to a user input.

In the parameter adjusting operation, at least one of power, a pulse duration, and a pulse period of RF energy may be adjusted.

An embodiment of the present disclosure may provide a mask pad including a pad sheet configured to be attached to a face; and at least one EMS electrode pad provided at a position corresponding to a facial muscle when the pad sheet is attached to the face, wherein the EMS electrode pad includes: a base having a plate-like shape; a plurality of electrodes arranged on a lower surface of the base; a plurality of first connection portions penetrating the base in a thickness direction and having one side electrically connected with each of the plurality of electrodes; and a second connection portion disposed on an upper surface of the base and connected with the other side of the plurality of first connection portions, wherein the plurality of electrodes are provided in virtual sections divided by a plurality of first virtual lines and a plurality of second virtual lines on the lower surface of the base, the first line forms a path directing toward an edge from a center portion of the lower surface of the base, and the second line is configured as an annular path based on which a center portion of the base is an inner side.

Meanwhile, the pad sheet may be configured such that the EMS electrode is exposed to a surface in contact with the face.

In addition, the EMS electrode pad may be provided at a position of the patch sheet in which at least one of Frontalis, Temporalis, Procerus, Orbicularis oculi, Lavator labii superioris, Zygomaticus, Masseter, Buccinator, Risorius, Platysma, Oibicularis oris, Depressor labii inferioris, and Depressor anguli oris may be stimulated.

Furthermore, the EMS electrode pad may be provided in plurality, and the plurality of EMS electrodes may be configured to independently perform electrical stimulation on each contacted muscle.

BRIEF DESCRIPTION OF THE DRAWINGS

FIG. 22 is a view showing a use state in the first, second, third, and fifth treatment modes.

DESCRIPTION OF EXEMPLARY EMBODIMENTS

Figure 1:
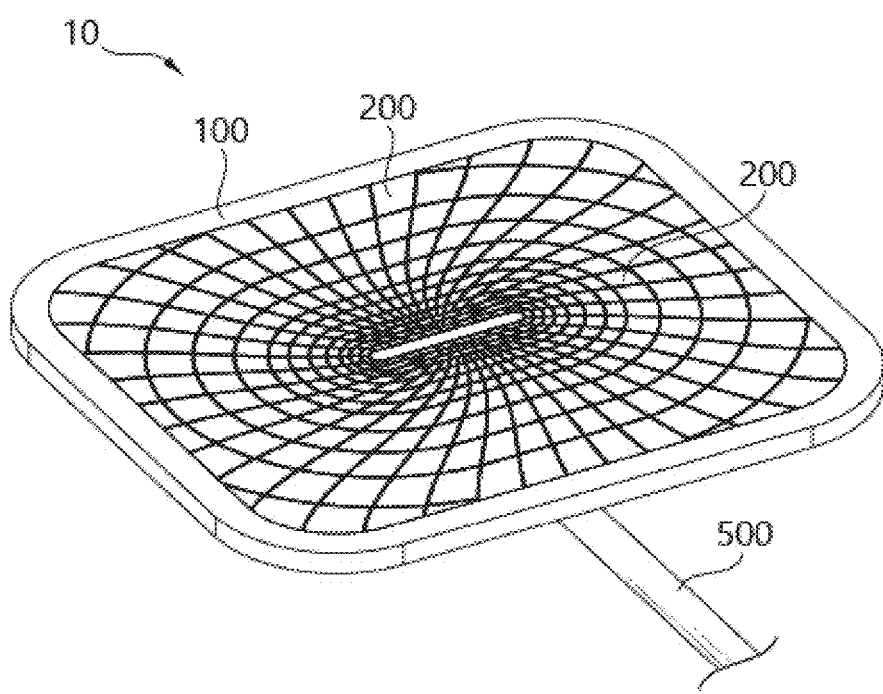
FIG. 1 is a perspective view showing an electrode pad according to a first embodiment of the present invention.

Hereinafter, an electrical muscle stimulation (EMS) electrode pad and an EMS mask pad comprising the EMS electrode pad and an EMS method using the same according to an embodiment of the present invention will be described in detail with reference to the accompanying drawings. In addition, in the description of the following embodiments, the names of each component may be referred to by other names in the art. However, if a modification is employed, when there are functional similarity and sameness, components thereof may be considered to be the same. In addition, reference numerals added to each component are used for convenience of description. However, the content illustrated on the drawings in which these reference numerals are indicated does not limit each component to the range within the drawings. Likewise, even if an embodiment in which some components in the drawings are partially modified is employed, if there is functional similarity and sameness, the components may be considered to be the same. In addition, in view of the level of a general technician in the relevant technical field, if a component is recognized as a component that should be naturally included, a description thereof will be omitted.

Hereinafter, a configuration of an electrical muscle stimulation (EMS) pad according to a first embodiment of the present invention will be described in detail with reference to FIGS. 1 to 4.

Figure 2:
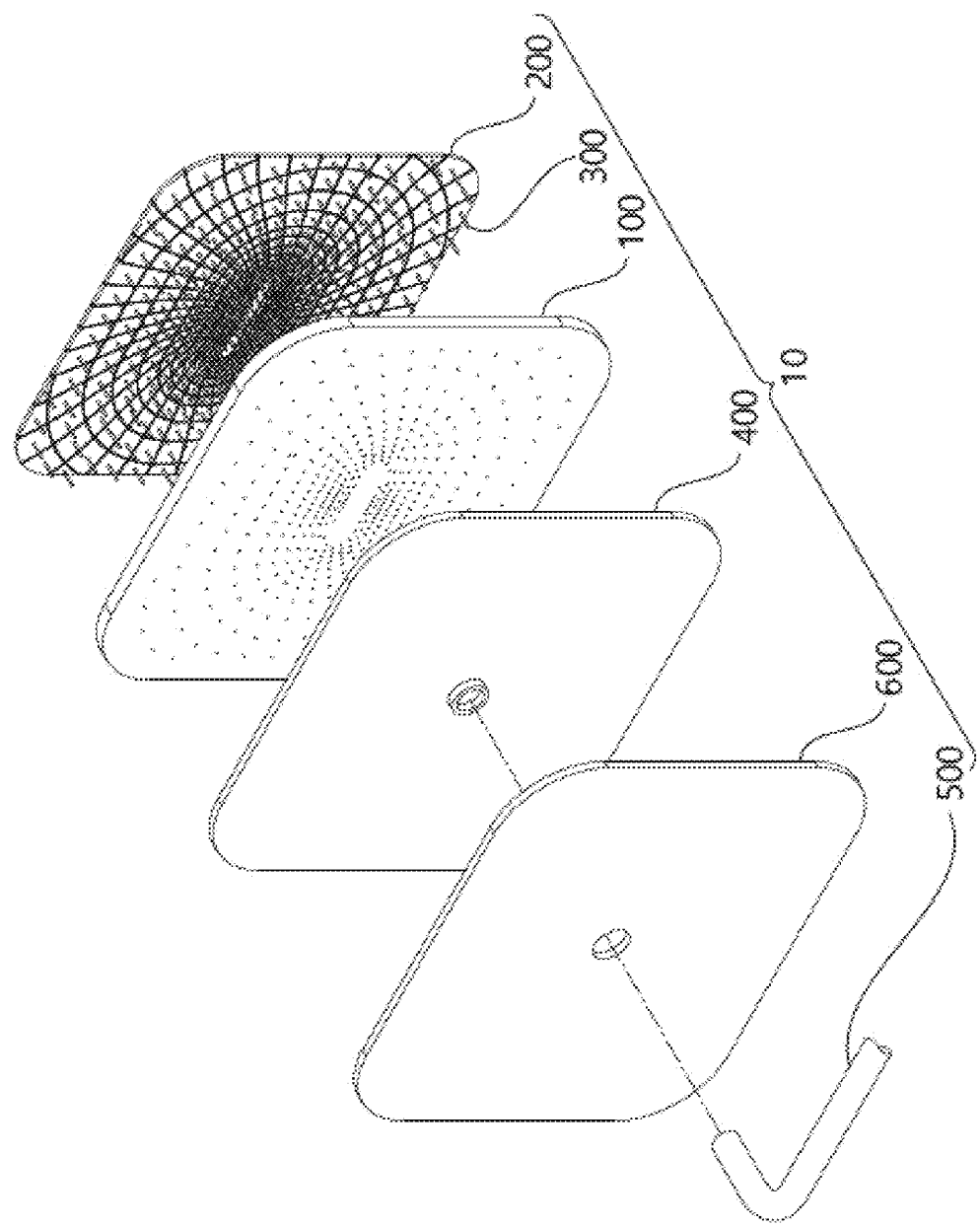
FIG. 2 is an exploded perspective view of an electrode pad according to the first embodiment of the present invention.

FIG. 1 is a perspective view showing an electrode pad according to the first embodiment of the present invention, and FIG. 2 is an exploded perspective view of the electrode pad according to the first embodiment of the present invention.

Referring to FIG. 1, the electrode pad 10 according to the first embodiment of the present invention may be configured to be attached to a skin surface and may receive RF energy from the outside in a state of being attached to the skin and transfer the received RF energy to the skin.

An electrode pad 10 according to the first embodiment of the present invention may include a base 100, an electrode 200, a first connection portion 300, a second connection portion 400, a shielding layer 600, and a connector 500.

The base 100 is a base on which the electrode 200, the first connection portion 300, and the second connection portion 400 are disposed. The base 100 may be entirely formed in a flat plate shape. The base 100 is configured in a flat plate shape having a large upper or lower surface in FIG. 1, and a plurality of electrodes 200 may be provided as a planar arrangement on the upper or lower surface. The base 100 may be formed of an insulating material so that current may not flow through the base 100 between the electrodes when the electrodes 200 to be described later are divided to be arranged and RF energy is applied from the outside.

Hereinafter, it is assumed that a plurality of electrodes 200 is provided on the lower surface 101 of the base.

The electrode 200 may configured to be airtightly in contact with a skin when transferring RF energy applied from the outside to the skin. Each electrode 200 having flat plate shape is configured such that an upper surface thereof is in contact with the base 100 and a lower surface thereof is in contact with the skin. Therefore, when the base 100 is in close contact with the skin, the plurality of electrodes 200 may be in contact with the skin at a plurality of points to transfer RF energy.

The electrode 200 is provided in plurality and the plurality of electrodes may be arranged in planar manner on the lower surface 101 of the base. The electrodes 200 may be disposed to be spaced apart from each other by a predetermined distance on the lower surface 101 of the base. Meanwhile, the planar arrangement and the shape of each electrode 200 will be described in detail later with reference to FIG. 3.

The first connection portion 300 is configured to be electrically connected to the plurality of electrodes 200 provided on the lower surface 101 of the base. The first connection portion 300 may be configured to penetrate the base 100 in a thickness direction, that is, from an upper surface to a lower surface. The first connection portion 300 is configured in the form of a pin and provided in a number corresponding to the number of the plurality of electrodes 200, so that the plurality of first connection portions may be electrically connected to the plurality of electrodes 200, respectively on one side thereof. As an example, the first connection portion 300 may be configured as a single member extending from the upper surface of each of the plurality of electrodes 200 by a predetermined length, and the predetermined length of each of the first connection portions 300 may be greater than a thickness of the base 100.

In this case, when the plurality of electrodes 200 are installed on the base 100, an upper end of the first connection portion 300 may be exposed on an upper surface 102 of the base. However, in the present embodiment, an example in which the first connection portion 300 is formed of a pin has been described, but the shape of the first connection portion 300 may be modified and applied as various components that may be electrically connected to each electrode 200.

The second connection portion 400 is configured to transfer RF energy applied from the outside to the plurality of first connection portions 300. The second connection portion 400 may be provided on the upper surface 102 of the base and may be configured to be electrically connected to upper ends of the plurality of first connection portions 300 described above at a plurality of points. The second connection portion 400 may be configured such that one side thereof is electrically connected to the connector 500 to be described later to receive RF energy from the outside. For example, the second connection portion 400 may be formed of a metal pad having a flat plate shape. In this case, a lower surface of the metal pad may be in close contact with the upper surface 102 of the base and may be electrically connected to the plurality of first connection portions 300 at a plurality of points. Meanwhile, an example in which the second connection portion 400 is formed of a metal pad has been described above, but the second connection portion 400 may be applied as various components such as an electrical element, e.g., a metal mesh, a metal wire, or the like which may be electrically connected to an end of the plurality of first connection portions 300 and receive RF energy from the outside.

The shielding layer 600 is configured to cover the second connection portion 400 exposed on the upper surface 102 of the base. The shielding layer 600 may be configured in the form of a film to cover the second connection portion 400 and may be configured to insulate the second connection portion 400 from the outside.

The connector 500 is configured to receive RF energy from the outside. The connector 500 may be provided on the upper surface 102 of the base, may be provided in a region exposed to the upper side of the shielding layer 600 so that one side thereof may be electrically connected to the second connection portion 400. For example, the connector 500 may be provided at a center portion of the upper side of the shielding layer 600, and one side thereof may be connected to the second connection portion 400 through the shielding layer 600. However, the configuration and installation position of the connector 500 described above are merely an example, and the connector 500 may be modified and applied as various components that may electrically connect the outside and the second connection portion 400.

Meanwhile, although not shown, the EMS electrode pad 10 may be connected with an RF energy generating device capable of generating RF energy such as an RF generator, an RF modulator, and an impedance matching circuit, so as to be used.

Hereinafter, the electrode 200 of the present embodiment will be described in detail with reference to FIGS. 3 and 4.

Figure 3:
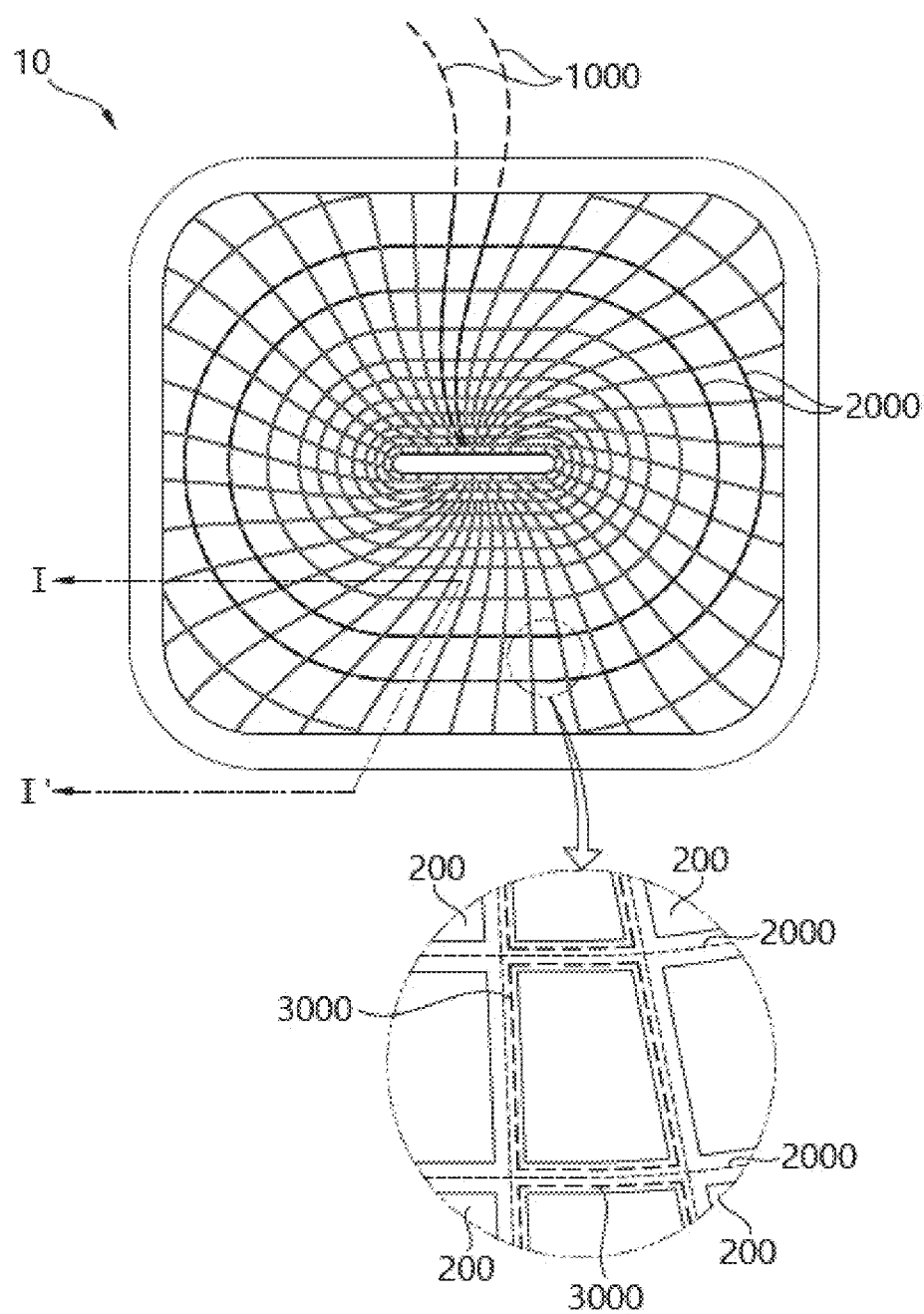
FIG. 3 is a bottom view of the electrode pad of FIG. 1.

FIG. 3 is a bottom view of the electrode pad 10 of FIG. 1. As shown, in the present embodiment, a plurality of electrodes 200 may be provided in sections 3000 divided on a lower surface of the base 100, respectively.

A lower surface 101 of the base may be divided into sections 3000 by a first virtual line 1000 and a second virtual line 2000. The first virtual line 1000 may be formed radially from a center portion of the base 100 toward an outer edge portion. The first virtual line 1000 may is provided in plurality, and the plurality of first virtual lines 1000 may be arranged to be spaced apart from each other at a predetermined angle in a rotation direction based on the center portion of the base 100. At least a portion of each of the first lines 1000 may be formed of a curved line. As an example, the first line 1000 may be configured to have curve in a sinusoidal wave-shape. In this case, each of the first lines 1000 may be formed to have a length shorter than one wavelength of the sinusoidal wave. That is, as shown in FIG. 3, one first line 1000 may have a length in which the sinusoidal wave waveform is not completed from the center portion of the base 100 to an outer rim of the base 100, that is, a length shorter than the wavelength.

The second virtual line 2000 may be formed along an annular path surrounding the center portion on the lower surface 101 of the base. As an example, the second virtual line 2000 may have a stadium shape as a whole, and may be configured to form a closed path. A plurality of second virtual lines 2000 are defined and formed concentrically with each other, and a space between the second virtual lines 2000 increases in a direction toward the outer edge of the base 100.

The electrodes tend to gradually decrease in size in a direction toward the center on the lower surface of the base. Here, a minimum size of the electrode may be limited. Thus, at least a portion of the center portion of the lower surface of the base may not have an electrode. However, this is only an example, and at least a portion of the center portion on the lower surface of the base may be modified and applied as a configuration in which electrodes having a uniform size are disposed.

The lower surface 101 of the base may be divided into a plurality of virtual sections 3000 by a plurality of first and second lines 1000 and 2000. A plurality of electrodes 200 may be arranged in the divided sections 3000 of the lower surface 101 of the base, excluding the first virtual line 1000 and the second virtual line 2000. Here, since the first line 1000 is configured in the shape of a sinusoidal wave, at least a portion of a boundary edge of each of a plurality of regions may be configured as a curved line.

Referring to a partially enlarged region of FIG. 3, a plurality of electrodes 200 may be arranged in sections 3000, respectively. A planar shape of the plurality of electrodes 200 may be determined to correspond to a shape of the section 3000 determined by the first line 1000 and the second line 2000. Here, since the first lines 1000 are arranged radially as a whole, a space between each of the first lines 1000 increases in a direction away from the center portion. Accordingly, the size of the plurality of electrodes 200 varies depending on the position at which the electrodes are arranged. As an example, as shown in FIG. 3, the size of the electrode 200 gradually increases in a direction toward the outer edge on the lower surface 101 of the base.

Figure 4:
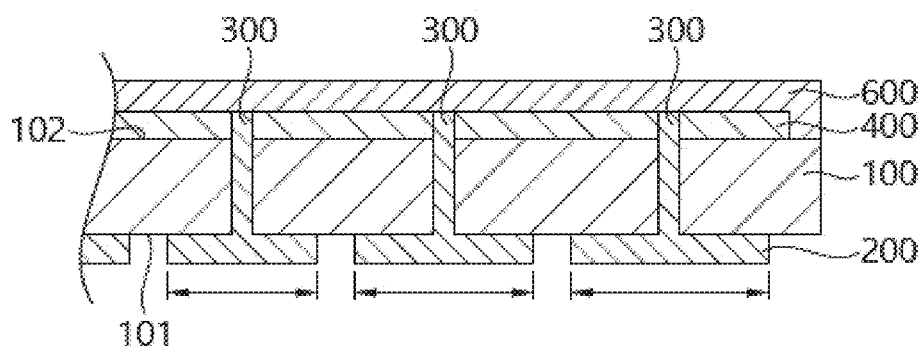
FIG. 4 is an enlarged cross-sectional view taken along line I-I' of FIG. 3.

FIG. 4 is an enlarged cross-sectional view taken along line I-I' of FIG. 3. As illustrated, a plurality of electrodes 200 different from each other may be provided on the lower surface of the base 100. One side of the first connection portion 300 may be connected to each electrode 200, the first connection portion 300 penetrate the base 100, and the other side thereof may be connected to the second connection portion 400. The shielding layer 600 may be provided on the second connection portion 400.

Meanwhile, the EMS electrode pad 10 according to the present invention described above may be entirely formed of a rigid material. When the EMS electrode pad 10 is formed of a rigid material, the EMS electrode pad 10 may be easily attached to a part of the skin with high flatness, such as the pectoralis major muscle and the thigh muscle.

Meanwhile, the EMS electrode pad 10 according to the present invention may be entirely formed of a flexible material. When the EMS electrode pad 10 is formed of a flexible material, it is possible to increase adhesion when the EMS electrode pad 10 is attached to the skin in order to stimulate a part of the skin with low flatness, for example, muscles in arms and calves.

Figure 5A:
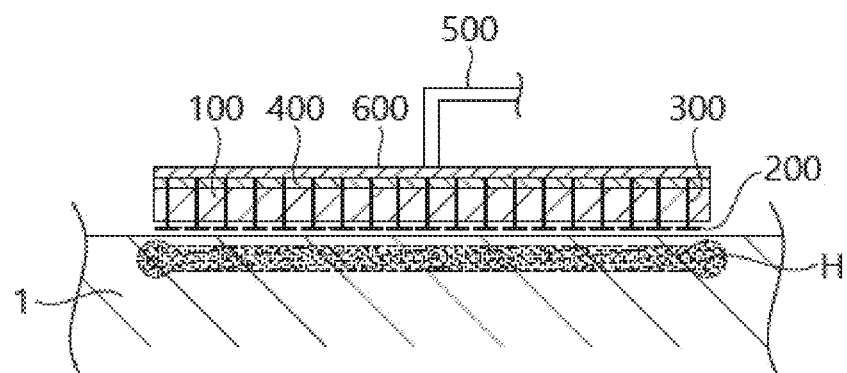
FIGS. 5A and 5B are a conceptual diagram showing a temperature distribution within a tissue when an electrode pad according to a first embodiment of the present invention is used.
Figure 5B:
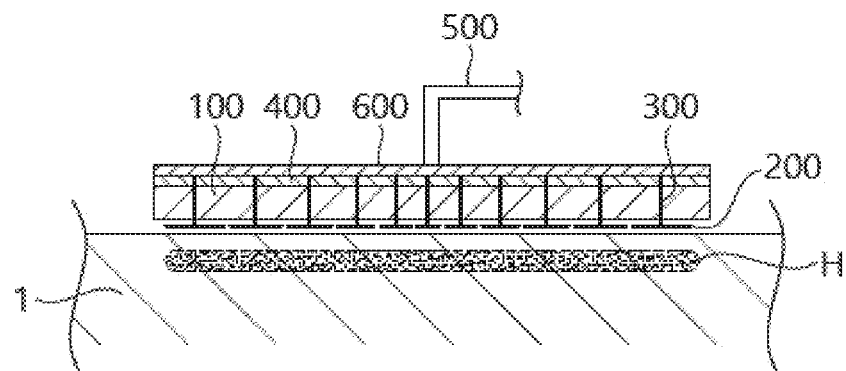

FIGS. 5A and 5B are a conceptual diagram showing a temperature distribution in a tissue 1 when the electrode pad 10 according to the first embodiment of the present invention is used.

Referring to FIG. 5A, when RF energy is applied using the EMS electrode pad 10, an edge effect in which current is concentrated on the edge portion occurs. When a muscle is stimulated by applying current, a phenomenon in which a heating portion H is unnecessarily concentrated due to a resistance component of the tissue 1 itself in a movement path of the current occurs. When the current is concentrated to flow in the tissue 1 by the edge effect, a temperature rises intensively in a part, causing a problem that damage and pain of the tissue 1 are increased.

Therefore, it is desirable to minimize the concentration of current and apply current uniformly to each part in a state where the electrode pad 10 is attached to the skin. Referring to FIG. 5B, according to the present invention, a size of the plurality of electrodes 200 gradually increases in a direction from the center portion toward the outer edge. In addition, since each electrode 200 is formed along a sinusoidal wave, which is a shape of the first line 1000, current may be uniformly applied as a whole. Eventually, the EMS electrode pad 10 according to the present invention has a difference in size of each electrode 200 and a difference in shape of each electrode 200, so that uniform current may be applied throughout when the plurality of electrodes 200 are simultaneously used in a state of being arranged. Therefore, it is possible to evenly distribute the heating portion H by RF energy in the tissue 1.

Meanwhile, the EMS electrode pad 10 according to the present invention stimulates the muscle upon receiving RF energy from the outside, and here, RF energy may be transferred in a monopolar or bipolar manner. In the case of transferring RF energy in the monopolar manner, a separate ground electrode may be used together. Meanwhile, when RF energy is configured to be transferred in the bipolar manner, the electrode pads 10 may be configured as a pair and may be simultaneously attached to the skin and used.

Hereinafter, an EMS electrode pad 10 according to a second embodiment of the present invention will be described in detail with reference to FIGS. 6 and 8.

This embodiment may also be configured to include the same components as those of the embodiment described above, and descriptions of the same components will be omitted to avoid redundancy and different components will be described.

Figure 6:
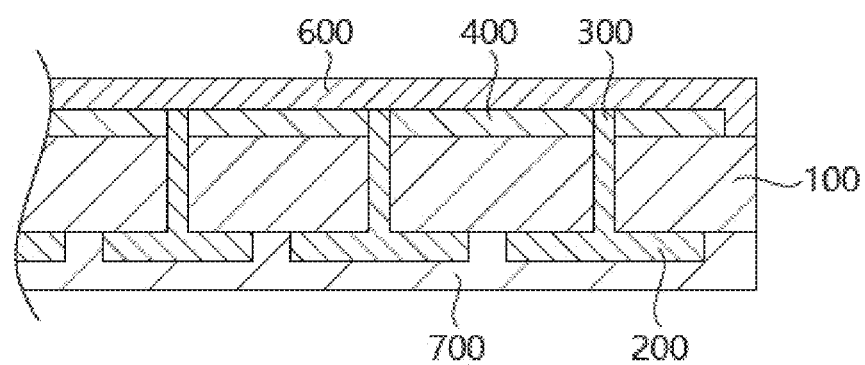
FIG. 6 is a partial cross-sectional view of an electrode pad according to a second embodiment of the present invention.

FIG. 6 is a partial cross-sectional view of the electrode pad 10 according to the second embodiment of the present invention. The second embodiment of the present invention may include a dielectric layer 700 covering a plurality of electrodes 200 provided on a lower surface 101 of a base.

The dielectric layer 700 is formed in a flat plate shape and may be configured to cover a plurality of electrodes 200 at the same time. The dielectric layer 700 may be formed of a material having a dielectric constant in a predetermined range. The dielectric layer 700 may be attached to each of the electrodes 200 such that an upper surface thereof covers the electrodes 200 and a lower surface thereof is attached to the skin. The dielectric layer 700 may be formed of a rigid or flexible material. As an example, the dielectric layer 700 may be formed of ceramic or polytetrafluoroethylene (PTFE).

Figure 7:
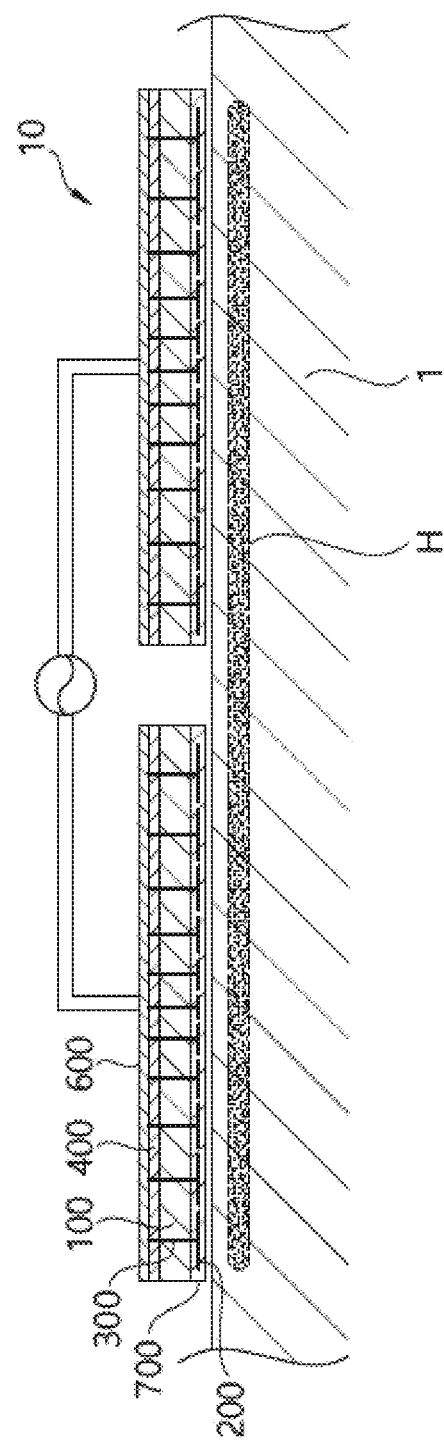
FIG. 7 is a conceptual diagram showing a state of use of an electrode pad according to a second embodiment of the present invention.

FIG. 7 is a conceptual diagram showing a use state of the electrode pad 10 according to the second embodiment of the present invention. In this embodiment, the concept of transferring RF energy in a bipolar manner is disclosed, and in this case, RF energy is transferred to stimulate the muscle in a state where a pair of EMS electrode pads 10 is attached to the skin. The muscle contracts as RF energy is transferred to the tissue 1 between the pair of EMS electrodes 200. Here, the RF energy may have a frequency of 2 to 10 NHrz, and it is possible to maximize electrical stimulation of the muscle, while distributing heating points in the tissue 1.

Here, when the lower surface of the EMS electrode pad 10 is coated with the dielectric layer 700, capacitive coupling may be formed between each electrode 200 and the skin. The dielectric layer 700 functions as a capacitor between the electrode 200 and the skin when RF energy is applied to the skin using the EMS electrode pad 10. As a result, since capacitive coupling is formed with the tissue 1 at the end of each electrode 200, an influence of parasitic capacitance may be minimized. In addition, it is possible to minimize an edge current in which an unintended overcurrent occurs in the electrode 200 disposed at the edge portion of the arrangement of the plurality of electrodes 200.

Figure 8:
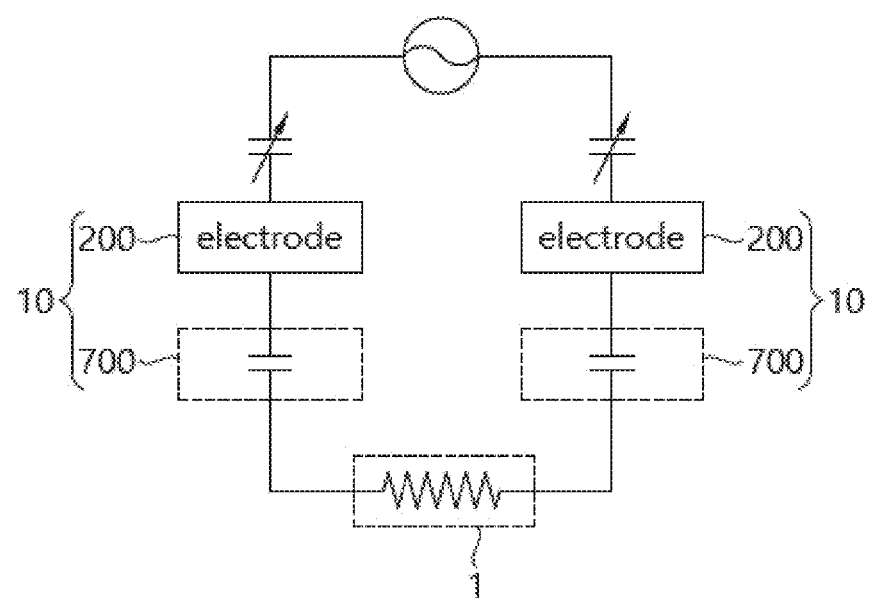
FIG. 8 is a conceptual diagram reconstructed from an electrical point of view when an electrode pad according to the second embodiment of the present invention is used.

FIG. 8 is a conceptual diagram reconstructed from an electrical point of view when the electrode pad 10 according to the second embodiment of the present invention is used.

Referring to FIG. 8, it is electrically connected so that RF energy may be transferred to the EMS electrode pad 10 from an external RF energy generating device. The EMS electrode pad 10 transfers RF energy through the plurality of electrodes 200, and here, each dielectric layer 700 functions as a capacitor in the tissue 1 expressed as a resistor. When RF energy is applied, impedance matching is performed using a variable capacitor or the like provided in the RF energy generating device, and here, accuracy of impedance matching may be improved by a capacitance component of the dielectric layer 700. After the impedance matching is completed, the RF energy generating device transfers RF energy to the EMS electrode pad 10, and RF energy is finally transferred to the tissue 1 to stimulate muscle.

Hereinafter, an electrode pad 10 according to a third embodiment of the present invention will be described in detail with reference to FIGS. 9 and 10. This embodiment may also be configured to include the same components as those of the embodiment described above, and descriptions of the same components will be omitted to avoid redundancy and different components will be described.

Figure 9A:
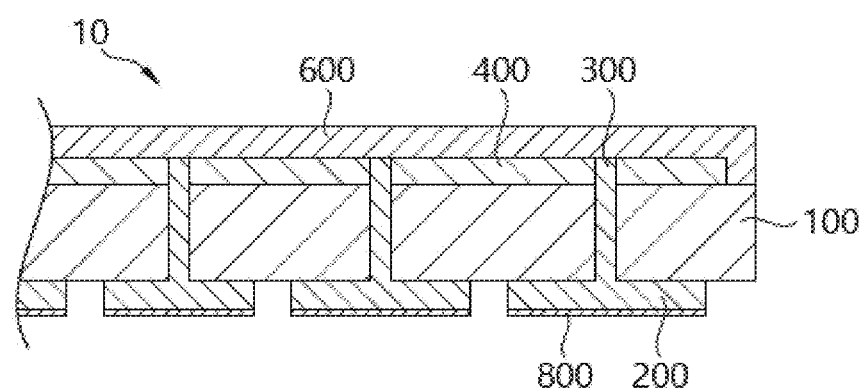
FIGS. 9A, 9B and 9C are an enlarged cross-sectional view of an electrode pad according to a third embodiment of the present invention.
Figure 9B:
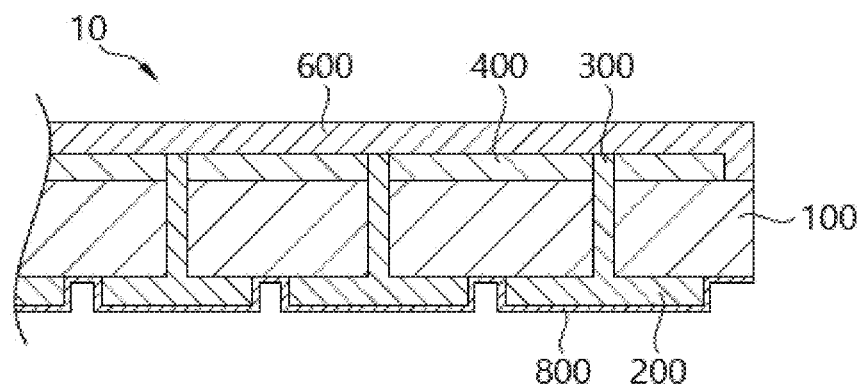
Figure 9C:
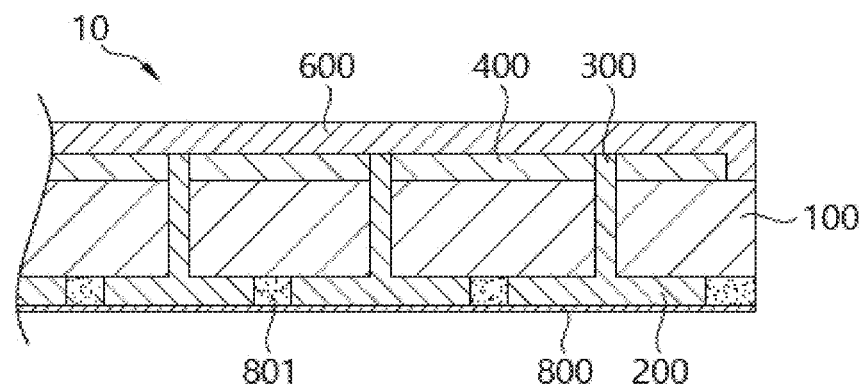

FIGS. 9A, 9B and 9C are an enlarged cross-sectional view of the electrode pad 10 according to the third embodiment of the present invention. Referring to FIGS. 9A, 9B and 9C, the EMS electrode pad 10 according to the third embodiment of the present invention may include a conductive layer 800 covering a plurality of electrodes 200. The conductive layer 800 may be configured to cover the lower surface of the electrode 200. As an example, the conductive layer 800 may be a graphene layer. Since graphene has high electrical conductivity and high elasticity, it may be appropriately deformed according to a curve of the skin, and thus, when the EMS electrode pad 10 is in close contact with the skin, the graphene layer may be deformed so as to be in close contact with the skin according to the curve of the skin, and in this state, RF current may be applied.

Graphene may be provided on the surface of the electrode 200 through a deposition process, a spray process, or a process of generating a corresponding graphene layer.

Referring to FIG. 9A, the graphene layer may be provided on the surface of each electrode 200, that is, on the lower surface of each of the plurality of electrodes 200. In this case, graphene may be deposited on a portion of the lower surface of the EMS electrode pad 10, that is, on the surface of the plurality of electrodes 200.

Referring to FIG. 9B, the graphene layer may be formed of a layer covering the plurality of electrodes 200. The graphene layer may be formed by providing a step difference between the plurality of electrodes 200 and the lower surface 101 of the base. Although it is shown that the graphene layer has an edge in the drawing, the grapheme layer may be formed to form a smooth curved surface on a boundary surface of the electrode 200.

Referring to FIG. 9C, an embodiment in which an insulating member 801 is provided between a plurality of electrodes 200 and a graphene layer is added in the EMS electrode pad 10 is illustrated. The insulating member 801 may fill a space between the electrodes 200 to minimize a step difference with the lower surface of the plurality of electrodes 200. Thereafter, the graphene layer is provided to cover the plurality of insulating members 801 and the plurality of electrodes 200 to cover the entire lower surface of the EMS electrode pad 10.

Figure 10:
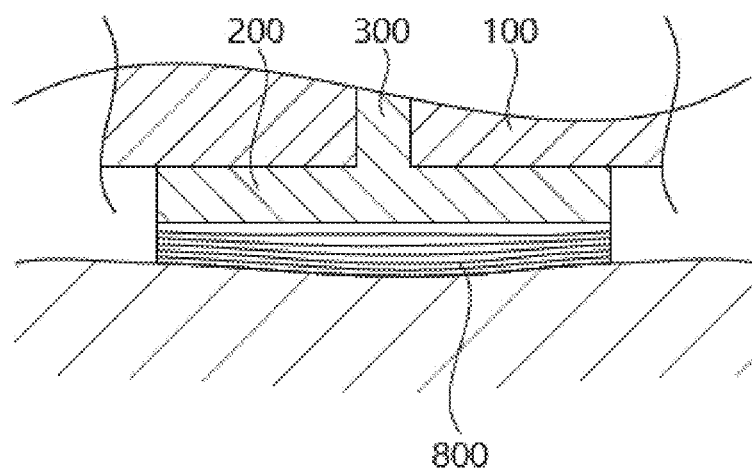
FIG. 10 is a conceptual diagram showing a state of use of an electrode pad according to the third embodiment of the present invention.

FIG. 10 is a conceptual diagram showing a state of use of the electrode pad 10 according to the third embodiment according to the present invention.

Referring to FIG. 10, the graphene layer may be formed in a single layer structure, and here, one graphene layer may be arranged and provided in a plane direction of the EMS electrode pad 10. In addition, the graphene layer may be formed in a multi-layer structure. In this case, an arrangement structure of each layer may be determined as a structure capable of maintaining high electrical conductivity between each graphene layer.

When a plurality of graphene layers are provided as described above, the EMS electrode pad 10 may be kept airtightly in contact with the skin surface. Specifically, when the plurality of graphene layers come into contact, a convex part of the skin is compressed in a thickness direction and a gap between the graphene layers is maintained in a concave part. Therefore, when the EMS electrode pad 10 is attached to the skin, a phenomenon that the contact is not made airtightly due to a partial curve of the skin so current is concentrated on a part the contact portion may be prevented. In other words, it is possible to reduce contact resistance between the skin and the plurality of electrodes 200 of the EMS electrode pad 10, thereby reducing edge current and uniformly applying current as a whole.

Hereinafter, an electrical muscle stimulation (EMS) method according to another embodiment of the present invention will be described in detail with reference to FIGS. 11 and 12.

Figure 11:
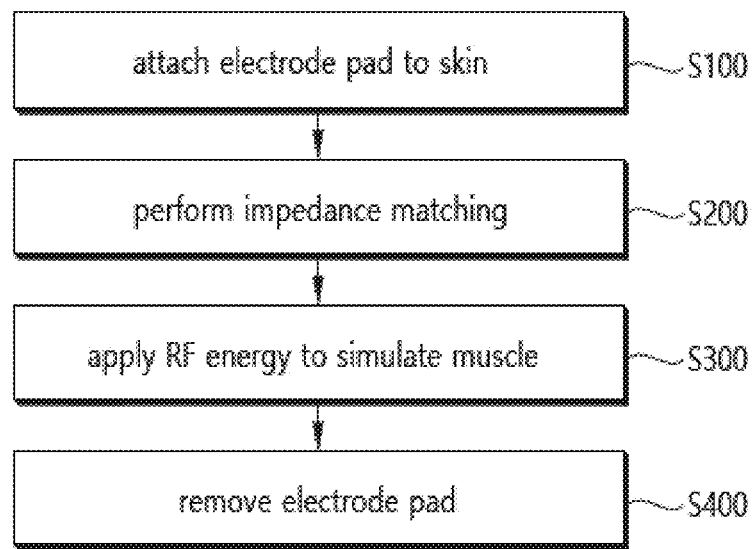
FIG. 11 is a flowchart an electrical muscle stimulation (EMS) method according to a fourth embodiment of the present invention.

FIG. 11 is a flowchart of the EMS method according to a fourth embodiment of the present invention.

Referring to FIG. 11, the EMS method according to the fourth embodiment of the present invention may include step (S100) of attaching the electrode pad 10 to the skin, step (S200) of performing impedance matching, step (S300) of transferring RF energy to simulate muscle, and step (S400) of removing the pad.

The step (S100) of attaching the electrode pad 10 to the skin corresponds to attaching the electrode pad 10 to the skin adjacent to the muscle to be stimulated. In the step S100 of attaching the electrode pad 10 to the skin, in the case of using monopolar RF energy, one electrode pad 10 and another ground electrode may be attached to the skin. Meanwhile, in the case of using bipolar RF energy, a pair of electrode pads 10 may be attached to the skin. In this case, the electrode pad 10 described above with reference to FIGS. 1 to 10 may be used as the electrode pad 10.

The step (S200) of performing impedance matching corresponds to performing impedance matching between the RF energy generating device, the electrode pad 10, and the skin so as to improve transfer efficiency of RF energy in a state where the electrode 200 is attached.

The step (S300) of transferring RF energy to stimulate muscle corresponds to generating RF energy and transmitting the RF energy to the muscle through the electrode pad 10. Here, the RF energy generating device may generate and transmit RF energy having a frequency of 2 to 10 MHrz. Meanwhile, as described above, since the electrode pad 10 includes the plurality of electrodes 200 whose shape is determined by the first line 1000 formed at least in part along the sinusoidal wave, edge current may be minimized when transferring RF energy using the plurality of electrodes 200. In addition, when a graphene layer is provided on the electrode pad 10, RF energy may be transferred to the skin through the electrode 200 and the graphene layer, in a state where the skin and the graphene layer are in close contact with each other.

The step (S400) of removing the pad corresponds to removing the pad after a predetermined electrical stimulation time expires and terminating the electrical muscle stimulation.

Figure 12:
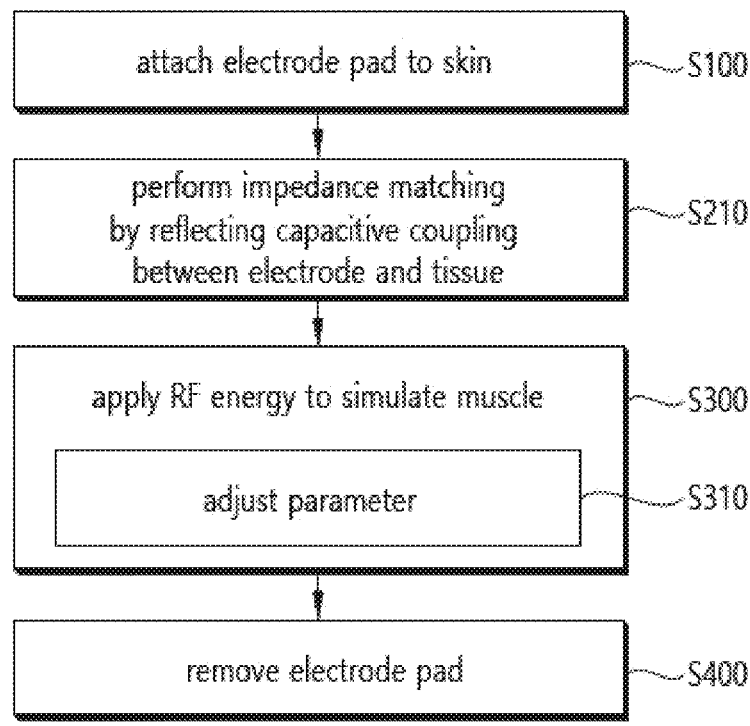
FIG. 12 is a flowchart of an EMS method according to a fifth embodiment of the present invention.

FIG. 12 is a flowchart of an EMS method according to a fifth embodiment of the present invention.

This embodiment may also be configured to include the same steps as those of the embodiment described above, and descriptions of the same steps will be omitted to avoid redundancy and different steps will be described.

In the present embodiment, electrical muscle stimulation when using the electrode pad 10 including the dielectric layer 700 will be described.

In step (s210) of performing impedance matching in the present embodiment, since the dielectric layer 700 provided on the lower surface of the electrode pad 10 functions as a capacitor, impedance matching is performed by reflecting capacitive coupling between the electrode and the tissue. In this embodiment, since capacitive coupling is formed between the plurality of electrodes 200 and the skin, accuracy of impedance matching may be improved.

The step (S300) of stimulating muscle by applying RF energy may include a parameter adjusting step (S310).

In the parameter adjusting step (S310), a parameter related to electrical muscle stimulation may be adjusted according to a user input. In the parameter adjusting step S310, a parameter for adjusting power, a pulse duration, and pulse period of RF energy may be selected. The RF energy generating device generates RF energy that may stimulate muscle according to an adjusted parameter value.

Figure 13:
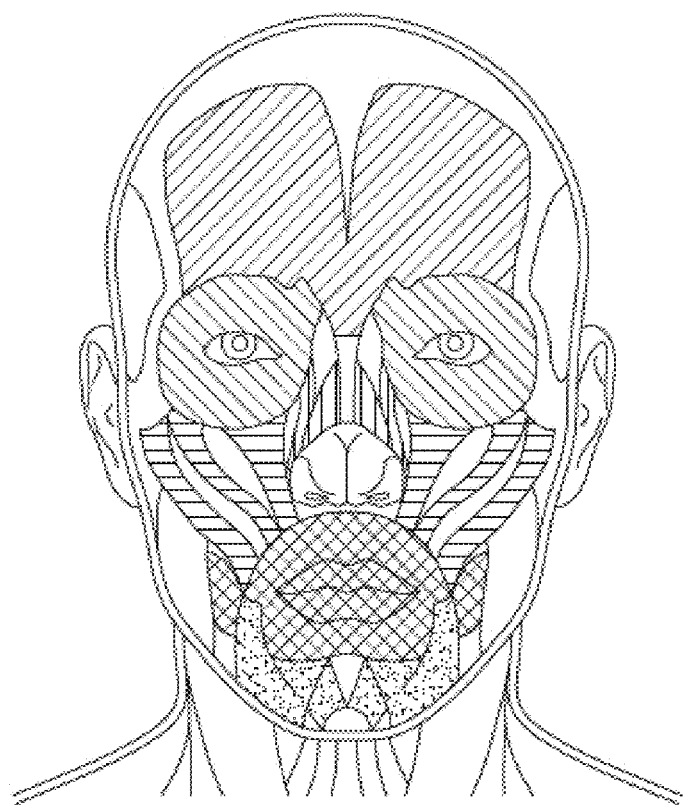
FIG. 13 is a view showing facial muscles.

FIG. 13 is a view showing facial muscles.

Referring to FIG. 13, there are various muscles on the face. The muscles of the face may typically cause a change in facial expression, movement of eyes, and movement of a mouth and a jaw.

Facial muscles may be classified forehead muscle group, orbital muscle group, nasal muscle group, oral muscles-upper group, oral muscle group, and oral muscles-lower group. Among the facial muscles, Frontalis belongs to the forehead muscle group, Orbicularis oculi belongs to the orbital muscle group, Procerus belongs to the nasal muscle group, Levator labii superioris, and Zygomaticus belong to the oral muscles-upper group, Risorius, Buccinator, and Platysma belong to the oral muscle group, Depressor labii inferioris and Depressor anguli oris belong to the oral muscles-lower group, and there are Masseter and Temporalis for chewing.

The muscles of the face are bilaterally symmetrical, and muscles that are frequently used are strengthened, like other muscles of the human body. Therefore, the facial muscles may be partially overdeveloped or asymmetrically developed. For example, due to a cause of weakening of part of the facial muscles due to nerve damage, the muscles may become relatively weak and develop asymmetrically. Meanwhile, the facial muscles may be developed by facial expressions that are frequently made and chewing habits. The development of these facial muscles may cause curves and wrinkles on the face. These curves and wrinkles on the face may give a psychologically positive or negative impression to a viewer. In addition, when the facial muscles develop to be bilaterally asymmetrical, functional effects may occur like a case of affecting a jaw joint. In this case, it is necessary to develop the facial muscles in a balanced manner.

The mask pad including the EMS electrode according to a sixth embodiment according to the present invention is configured to strengthen or treat facial muscles.

Figure 14:
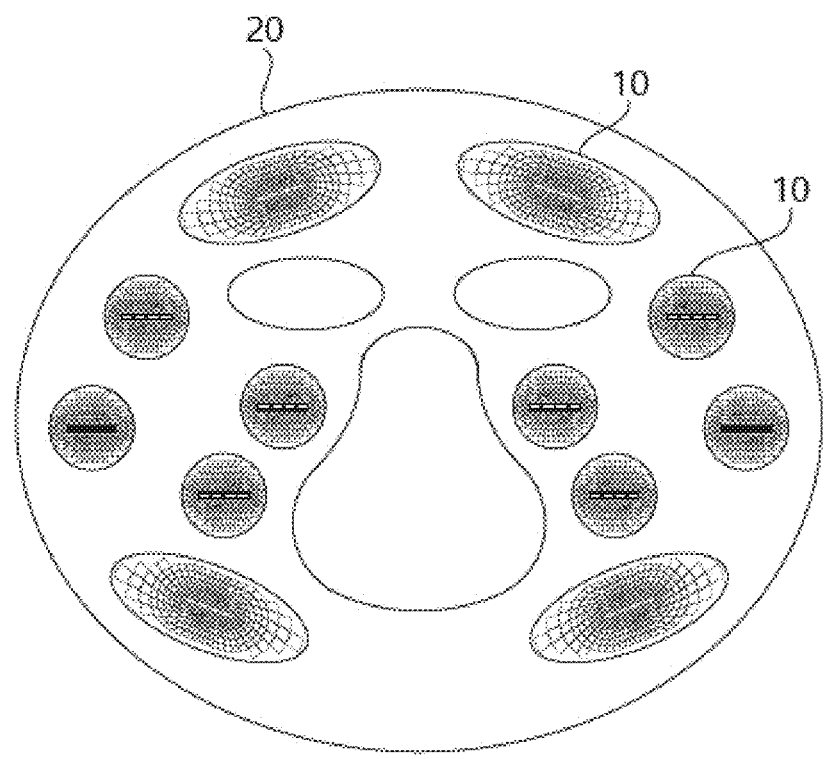
FIG. 14 is a front view of a mask pad including an EMS electrode according to the sixth embodiment of the present invention.

FIG. 14 is a front view of a mask pad including an EMS electrode according to the sixth embodiment of the present invention.

Referring to FIG. 14, the mask pad including an EMS electrode according to the sixth embodiment may include a pad sheet and an EMS electrode.

The pad may be configured to be slightly thin so as to be attached to the face and may be formed in a circular shape corresponding to the shape of the face. In addition, the pad sheet may have holes at positions corresponding to the eyes and nose to minimize discomfort when the user attaches the mask pad on the face to use the mask pad.

As described above, the EMS electrode may be formed to be divided into sinusoidal (or spiral) paths. The muscles of the face include relatively small muscles compared to other muscles of the human body. In addition, since the nerves of the facial muscles are somewhat complicatedly connected, side effects may occur due to electrical stimulation. In particular, such side effects may increase when current does not flow evenly to a part intended by the user and is concentrated on one place. As an example, side effects may occur in tissues adjacent to the edge of the electrode due to the aforementioned edge effect. However, EMS electrode of the present invention may maximize a treatment effect by stimulating the facial muscles, while minimizing such an edge effect.

At least one EMS electrode may be provided on a surface of the pad sheet in contact with the face. In an embodiment, the EMS electrode may be provided in plurality and may be provided at bilaterally symmetrical positions. Here, the EMS electrodes may be located at a position that may stimulate at least one of Frontalis, Temporalis, Procerus, Orbicularis oculi, Lavator labii superioris, Zygomaticus, Masseter, Buccinator, Risorius, Platysma, Oibicularis oris, Depressor labii inferioris, and Depressor anguli oris. FIG. 14 illustrates an example in which EMS electrodes are provided at positions for stimulating Frontalis, Levator labii superioris, Zygomaticus, Masseter, Temporalis, and Depressor anguli oris. The size of each EMS electrode may be determined according to a size (area) of the muscle to be stimulated.

One or more EMS electrodes provided on the pad sheet may be configured to individually perform electrical stimulation according to a user selection. That is, each electrode may be configured such that RF energy is independently transferred thereto.

Figure 15:
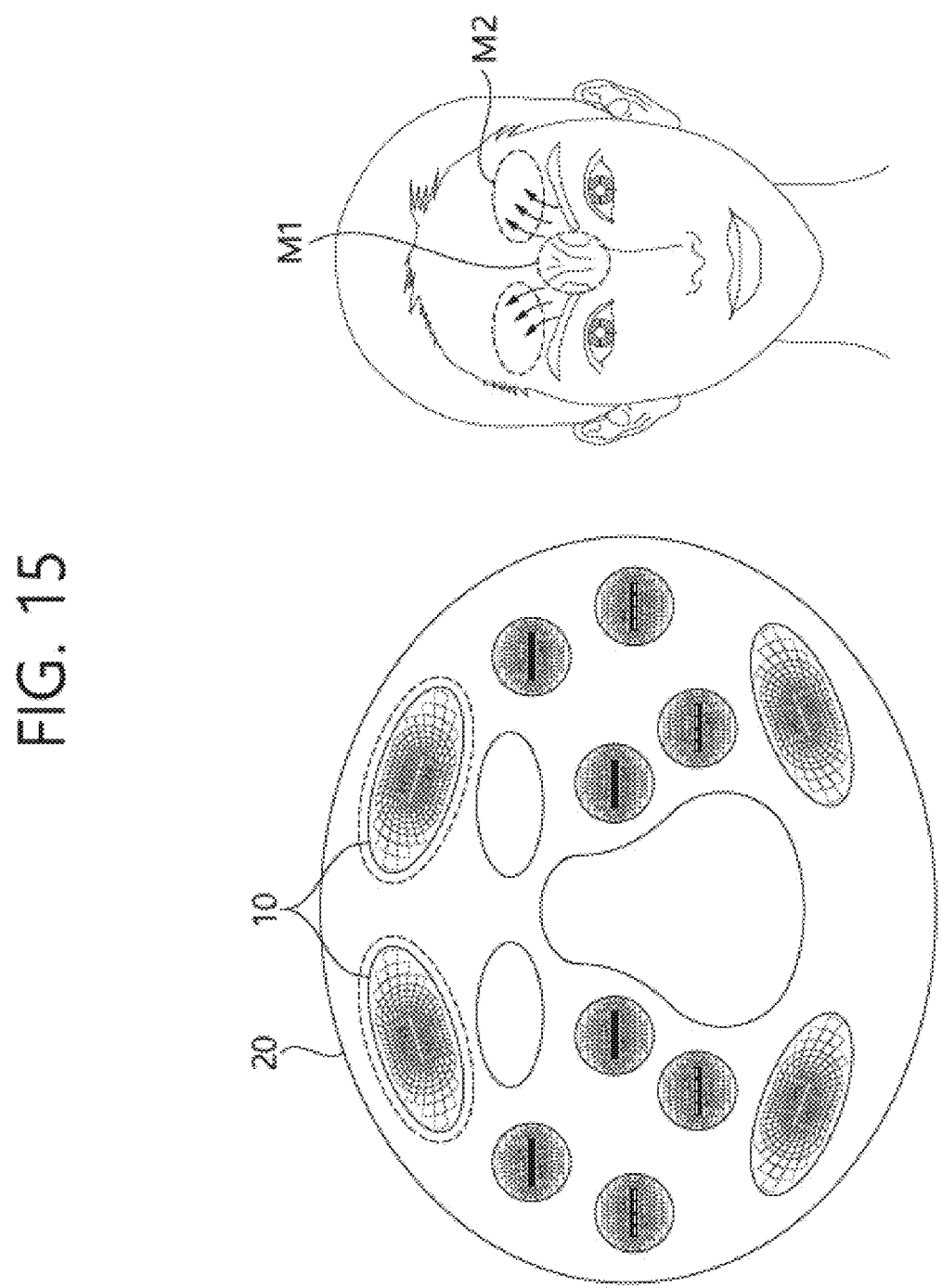
FIG. 15 is a state diagram of use of the sixth embodiment.

FIG. 15 is a state diagram of use of the sixth embodiment.

Referring to FIG. 15, a state in which wrinkles are excessively formed in a patient's brow is illustrated. Such wrinkles may occur due to excessive use and development of specific muscles as described above. In this case, a wrinkle improvement effect may be exerted by stimulating and strengthening the muscles that move in a direction in which wrinkles may be spread. As an example, the Procerus (M1) may develop excessively, and in this case, electrical simulation may be performed on the Frontalis (M2) by selecting the uppermost EMS electrode in a state in which the mask pad is attached to the face. Through electrical stimulation, an effect of wrinkle improvement may be exerted by relaxing Procerus (M1) excessively developed and contracted as muscles are strengthened due to repetitive contraction of Frontalis (M2). Such an electrical stimulation treatment may be achieved through a substantial increase in muscle mass multiple times.

As described above, with the EMS electrode pad and the EMS mask pad comprising the EMS electrode pad and the EMS method using the same according to the present invention, accuracy of impedance matching may be improved when stimulating muscles using RF energy, thereby improving control accuracy of RF energy transfer. Also, the occurrence of edge current may be minimized and RF energy may be transferred evenly for each part. As a result, it is possible to prevent the occurrence of an unnecessary hot spot when RF energy is transferred to the skin tissue.

The EMS electrode pad and the EMS mask pad comprising the EMS electrode pad and the EMS method using the same according to the present invention may minimize the edge current effect by the shape of the electrode to which electric energy is applied. In addition, energy transfer efficiency may be improved by capacitive coupling between the electrode and the skin. In addition, due to the coating of the electrode, a rate of contact with an affected part may be increased so that current may be applied evenly to each part.

Hereafter, an apparatus of muscle treatment including an EMS electrode, a method of controlling the apparatus, and a method of muscle treatment using the apparatus according to an embodiment of the present disclosure are described in detail with reference to FIGS. 16 to 27.

Figure 16:
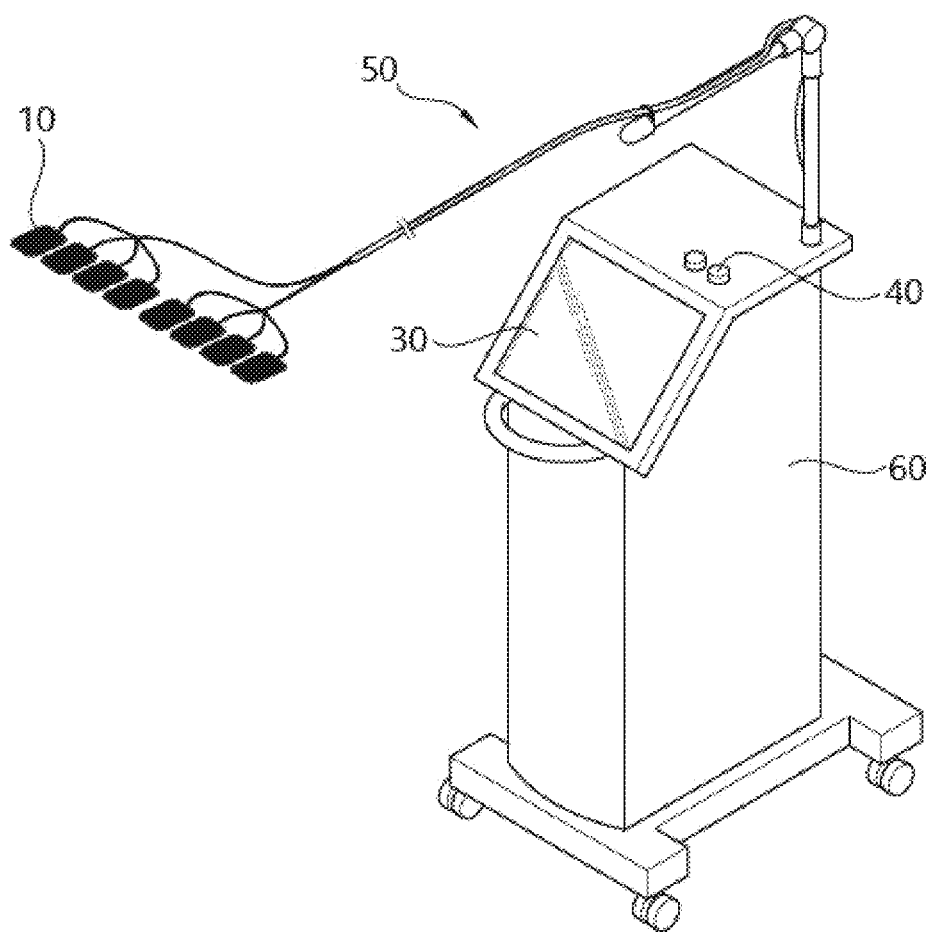
FIG. 16 is a perspective view of an apparatus of muscle treatment including an electrical muscle stimulation (EMS) electrode according to an embodiment of the present disclosure.

FIG. 16 is a perspective view of an apparatus of muscle treatment including an electrical muscle stimulation (EMS) electrode according to an embodiment of the present disclosure.

Referring to FIG. 16, an apparatus of muscle treatment comprising an EMS electrode according to an embodiment of the present disclosure may include a body 60, an RF generator (not shown), an RF modulator (not shown), an EMS electrode pad 10, a display 30, an input unit 40, a controller (not shown), and a cable 50.

The body 60 is a base for enabling other components to be provided. The body may be configured in a structure having a space therein and may include the RF generator, the RF modulator, and the controller therein. Though not shown, the embodiment may include the configuration of various electrical circuits and a power configuration such as an impedance matching circuit for operating the apparatus of muscle treatment. However, the electrical circuits and the power configuration are widely used, the detailed description is omitted.

The RF generator may generate RF energy that is sued for muscle treatment and the RF modulator may adjust the generated RF energy. The RF modulator may adjust the output of RF energy, that is, a frequency, an amplitude, and a voltage in response to a control input from the controller to be described below. It has been known that the effective frequency band for muscle stimulation is 50 KHz or less. In particular, it has been known that about 38 KHz is effective for relatively large muscles such as a quadriceps femoris muscle and a pectoralis major. On the contrary, it has been known that a frequency between 38 KHz and 50 KHz is effective for small muscles such as facial muscles. RF energy selected from the frequencies described above can be applied to the EMS electrode pad by the RF generator and the RF modulator.

The EMS electrode pad 10 may include a plurality of split electrodes, as in the embodiment described above, may include a plurality of split electrodes separated along a sinusoidal or spiral path, and may be configured such that the sizes of the spilt electrodes gradually increase outward from the center. Accordingly, it is possible to minimize an edge effect when applying RF energy to a tissue.

The EMS electrode pad 10 is provided as a plurality of pieces each of which may receive RF energy. The EMS electrode pads 10 may apply stimulation respectively to a plurality of muscles which are anatomically distinguished. The attachment positions may be selected by a user.

The display 30 and the input unit 40 may enable a user to perform and monitor operation for treatment. A user can operate parameters related to treatment such as a treatment mode, a treatment position, treatment intensity, and treatment time through the display 30 and the input unit 40. The display 30 and the input unit 40 may be modified in various configurations such as a touchable display.

The controller may control the general operation of the apparatus of muscle treatment. It is possible to adjust the RF energy that is applied to the EMS electrode pads in accordance with a treatment selected by input from a user, and input such as start of treatment, urgent stop during treatment, a change of a parameter during treatment, and a change of a treatment mode during treatment. The controller can determine EMS electrode pads attached to a skin of the plurality of EMS electrode pads, can prevent RF energy from being applied to electrode pads determined as not being attached to a skin, and can inform a user of EMS electrode pads that are not visually in contact. The controller can control the RF generator and the RF modulator such that RF energy can be independently applied to the EMS electrode pads.

The cable 50 may connect the body and the EMS electrode pads. The pad is provided as a plurality of pieces to be able to connect the EMS electrode pads and the body, respectively. The body may be connected with the RF modulator, the controller, and the RF generator in the cables.

Hereafter, a process of applying RF energy by the apparatus for muscle treatment including an EMS electrode pad in accordance with treatment modes is described in detail with reference to FIGS. 17 to 25. The treatment modes can be anatomically distinguished and can be applied to at least two muscles related to each other in the following description. The muscles related to each other mean muscles generating movement of a human body in accordance with two kinds of muscles between one or two joints.

The controller includes control algorithms for a first treatment mode to a fifth treatment mode and can perform control in accordance with selection of a user.

Figure 17:
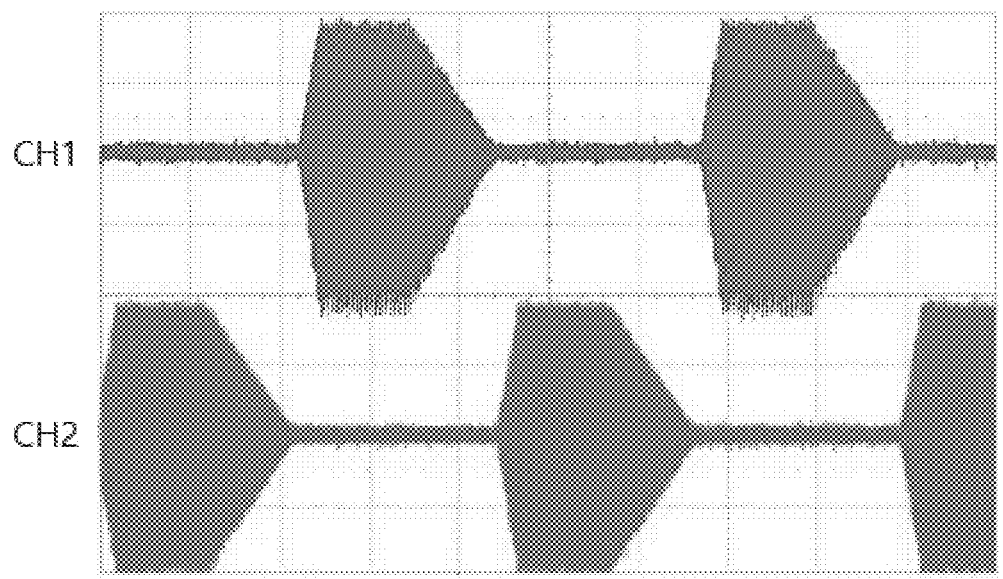
FIG. 17 is a graph showing an application pattern of RF energy applied in a first treatment mode.

FIG. 17 is a graph showing an application pattern of RF energy applied in a first treatment mode.

Referring to FIG. 17, a first treatment mode is configured to control RF energy to be able to alternately generate contraction and relaxation for at least two muscles related to each other. In the first treatment mode, a fundamental energy application pattern is one single unit pattern showing four types of control composed of an increase of an amplitude, maintenance of an amplitude, a decrease of an amplitude, and interception of RF energy. A muscle contracts from a relaxed state in a period for which as RF energy is applied, the amplitude increases, which is a first transition period. The muscle maintains the contracted state in a period for which the amplitude of the RF energy is maintained, which is a maintenance period. Thereafter, the muscle relaxes from the contracted state in a period for which the amplitude of the RF energy decreases, which is a second transition period. Thereafter, the muscles rest in a period for which the RF energy is intercepted, which is a rest period. Accordingly, RF energy is applied with one unit pattern, the muscle receiving the RF energy shows four steps of movement of contraction-maintenance-relaxation-rest.

The first transition period for which the muscle contracts may be set shorter than the second transmission period for which the muscle relaxes. This is for generating movement of the muscle similar to the actual process of exercising of modern people for increasing the amount of muscles. Accordingly, when RF energy is applied to a muscle in accordance with a unit pattern, the muscles undergoes a process of quick contraction, maintenance, slow relaxation, and rest.

Referring to FIG. 17 again, RF energy is applied with a unit pattern alternately from a first channel and a second channel respectively connected to EMS electrode pads attached to different muscles. The two muscles related each other alternately undergo contraction-maintenance-relaxation-rest.

Figure 18:
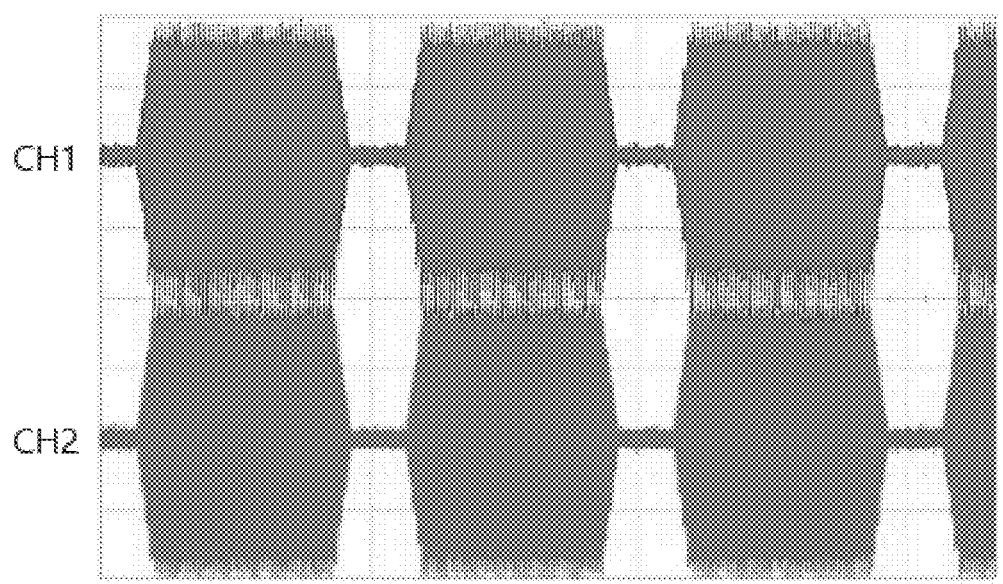
FIG. 18 is a graph showing an application pattern of RF energy applied in a second treatment mode.

FIG. 18 is a graph showing an application pattern of RF energy applied in a second treatment mode.

Referring to FIG. 18, the second treatment mode controls RF energy such that at least two muscles related to each other can simultaneously contract and relax. In this case, unit patterns are simultaneously shown at the first channel and the second channel. In this case, the amplitudes of RF energy applied to the channels are also determined at similar levels.

Figure 19:
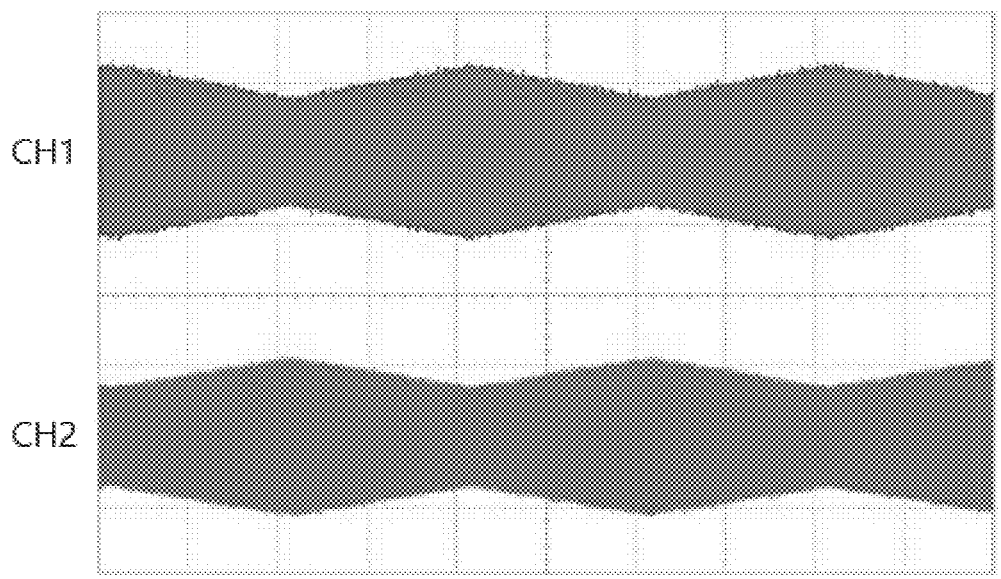
FIG. 19 is a graph showing an application pattern of RF energy applied in a third treatment mode.

FIG. 19 is a graph showing an application pattern of RF energy applied in a third treatment mode.

Referring to FIG. 19, the third treatment mode is configured such that a maintenance period and a rest period are omitted and the first transition period and the second transition period can be alternately shown in the unit pattern described above. The third treatment mode applies RF energy such that the transition period and the second transition period can be alternately shown in muscles related to each other.

Figure 20:
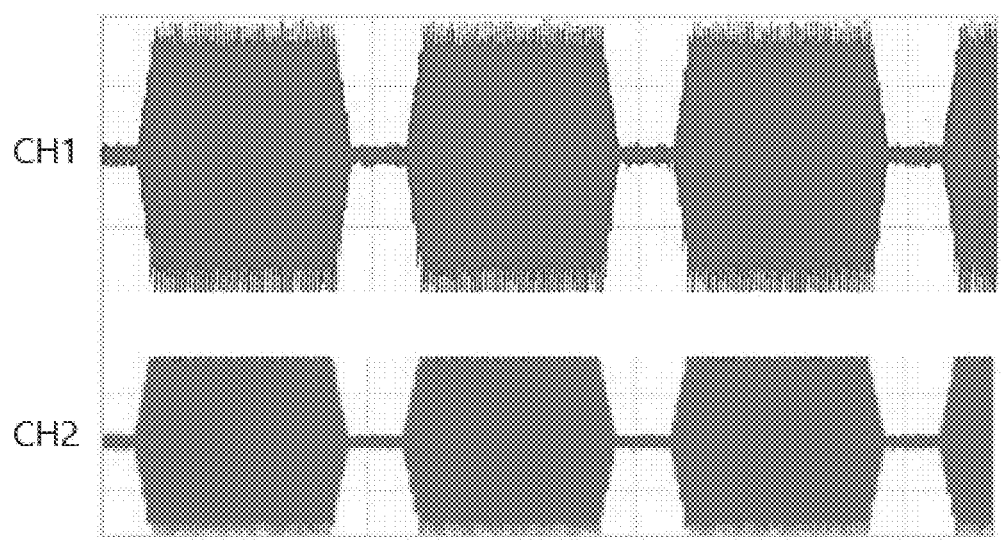
FIG. 20 is a graph showing an application pattern of RF energy applied in a fourth treatment mode.

FIG. 20 is a graph showing an application pattern of RF energy applied in a fourth treatment mode.

Referring to FIG. 20, the fourth treatment mode is configured to be able to generate a weight effect. The weight effect may be generated in muscles showing opposite movements with respect to one bone. For example, two muscles may be elected from the extensor muscle and the flexor muscle. In detail, in an arm, the extensor muscle may be triceps and the flexor muscle may be biceps. As another embodiment, in a leg, the extensor muscle may be one of the rectus femoris, vastus intermedius, vastus medialis, and vastus lateralis, and the flexor muscle may be one of the biceps femoris, semitendinosus, and semimembranosus.

The fourth treatment mode may be applied to muscles related to each other described above, in detail muscles moving a bone in opposite directions. The fourth treatment mode is similar to the second mode in terms of repeatedly applying a unit pattern and applying RF energy simultaneously to the first channel and the second channel in accordance with a unit pattern. However, in the fourth treatment, a main muscle and an auxiliary muscle are selected and the main muscle is usually contracted such that opposite resistance is generated in the auxiliary muscle. In this case, RF energy that is applied to the main muscle is applied with first power and is applied with second power smaller then the power of the RF energy that is applied to the auxiliary muscle. The larger the difference between the first power and the second power, the smaller the force against contraction of the main muscles, so the weight effect decreases. On the contrary, the smaller the difference between the first power and the second power, the larger the resisting force in the auxiliary muscle, so resistance is generated in contraction of the main muscles. The fourth treatment mode, similar to the effect of lifting a weight when a person actually exercises, can give an effect like lifting a weight by simultaneously generating electrical stimulation in a muscle to be strengthened and a muscle generating opposite movement.

A user can set a parameter in accordance with input and the different between the first power and the second power may be determined in accordance with a parameter value. Since the first power is power for stimulating the main muscle, it is effective to adjust the second power in accordance with a parameter.

Figure 21:
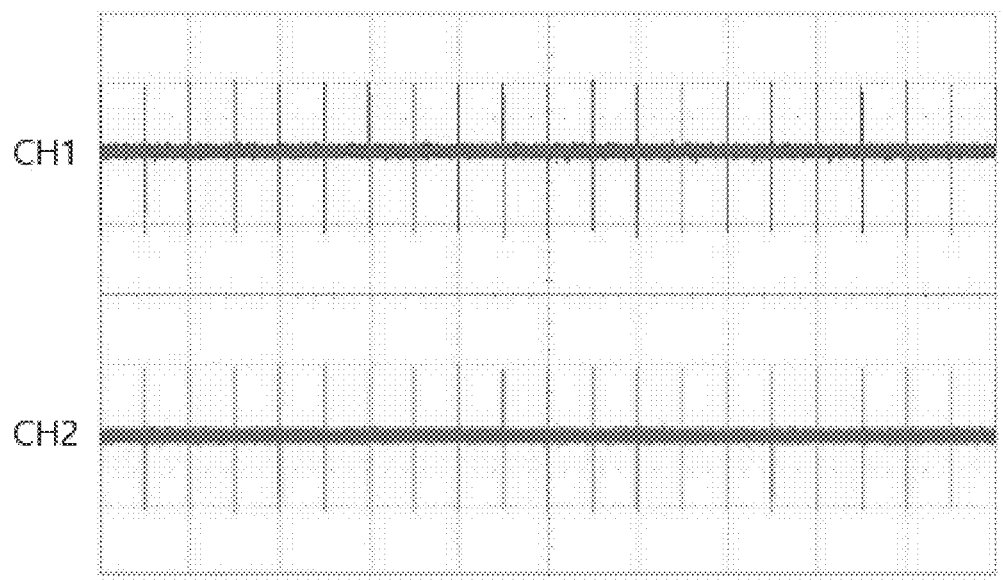
FIG. 21 is a graph showing an application pattern of RF energy applied in a fifth treatment mode.

FIG. 21 is a graph showing an application pattern of RF energy applied in a fifth treatment mode.

Referring to FIG. 21, the fifth treatment mode simultaneously applies impulse type of RF energy to the first channel and the second channel. Spring movement due to contraction of a muscle such as tapping may be generated. The fifth treatment mode may be performed to stabilize a muscle after the first to fourth treatment modes described above are performed.

Hereafter, an example of using the apparatus of muscle treatment including an EMS electrode pad according to an embodiment of the present disclosure is described with reference to FIGS. 22 to 25.

FIG. 22 is a view showing a use state in the first, second, third, and fifth treatment modes.

Referring to FIG. 22, an example of selecting and treating the abdominal muscles as muscles that can be anatomically distinguished and are related to each other is shown. In this case, it is possible to generate contraction of the muscles in accordance with a specific pattern by independently applying RF energy to four EMS electrode pads using four channels.

In detail, in a patient, it is possible to apply RF energy to EMS electrode pads respectively attached to the left upper straight muscle of abdomen through a first channel, the right upper straight muscle of abdomen through a second channel, the left upper external oblique muscle of abdomen through a third channel, the right upper external oblique muscle of abdomen through a fourth channel, the left lower straight muscle of abdomen through a fifth channel, the right lower straight muscle of abdomen through a sixth channel, the left lower external oblique muscle of abdomen through a seventh channel, and the right lower external oblique muscle of abdomen through an eighth channel.

A first treatment mode synchronizes the first channel and the fifth channel, the second channel and the sixth channel, the third channel and the seventh channel, and the fourth channel and the eighth channel, and applies RF signal. The first treatment mode applies RF energy simultaneously to the first channel and the fifth channel and applies RF signal simultaneously to the fourth channel and the eighth channel, thereby alternately generating contraction. As a result, the body may twist to the right.

The motion of twisting the body to the opposite side is generated by applying RF signal simultaneously to the second channel and the sixth channel and then applying RF signal simultaneously to the third channel and the seventh channel.

It is possible to generate holding that keeps a body bent, gripping that tightening the body, and tapping by synchronizing the eight channels and selecting a treatment mode.

The treatment modes described above may be selected by a user, or a sequence for the first, second, third, and fifth treatment mode may be stored in accordance with a predetermined order and automatically performed.

Figure 23:
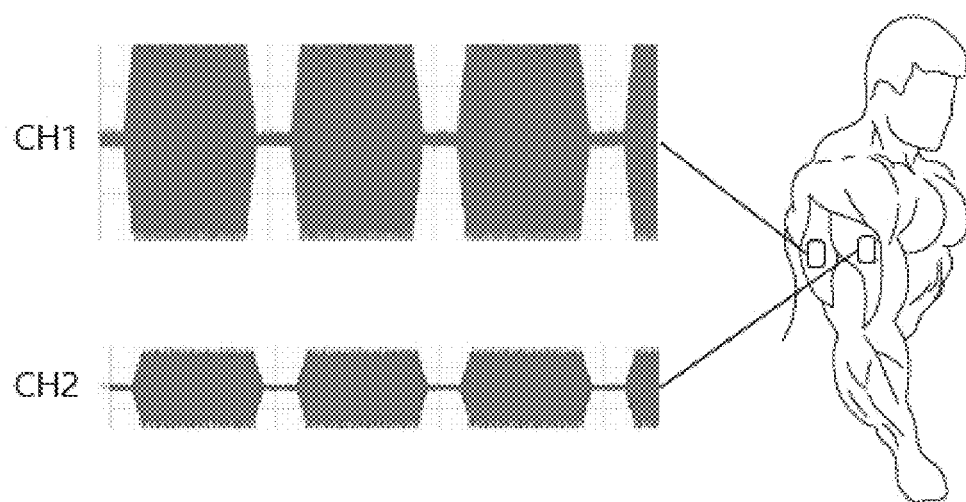
FIGS. 23 and 24 are views showing a use state when the fourth treatment mode is applied to an arm.
Figure 24:
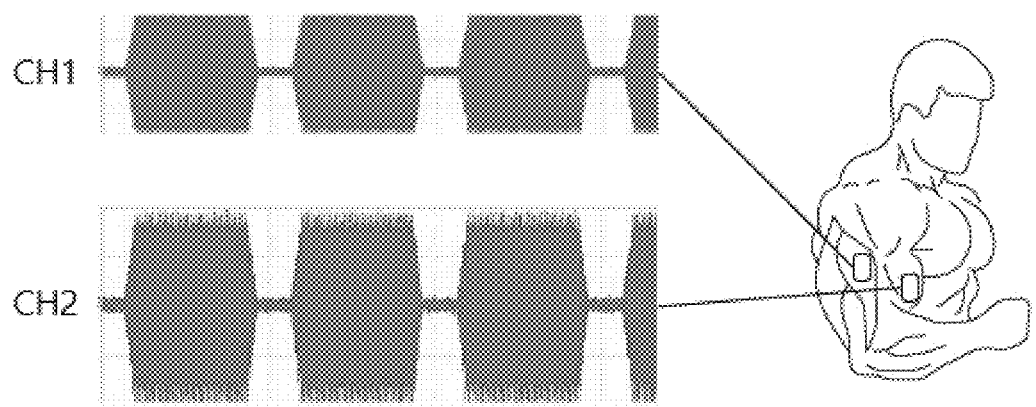

FIGS. 23 and 24 are views showing a use state when the fourth treatment mode is applied to an arm.

Referring to FIG. 23, which shows a concept when triceps are set as main muscles, RF energy is applied to the first channel, biceps are set as auxiliary muscles, and RF energy is applied from the second channel. As a weight effect in the fourth treatment mode, the main muscles are intensively stimulated by applying RF energy with first power and the auxiliary muscles are stimulated by RF energy with second power, whereby resistance is generated and the arm is stretched. In this case, resistance is generated by the auxiliary muscles when the main muscles are contracted by intensive stimulus, an effect like lifting a weight using the triceps is generated.

Figure 25:
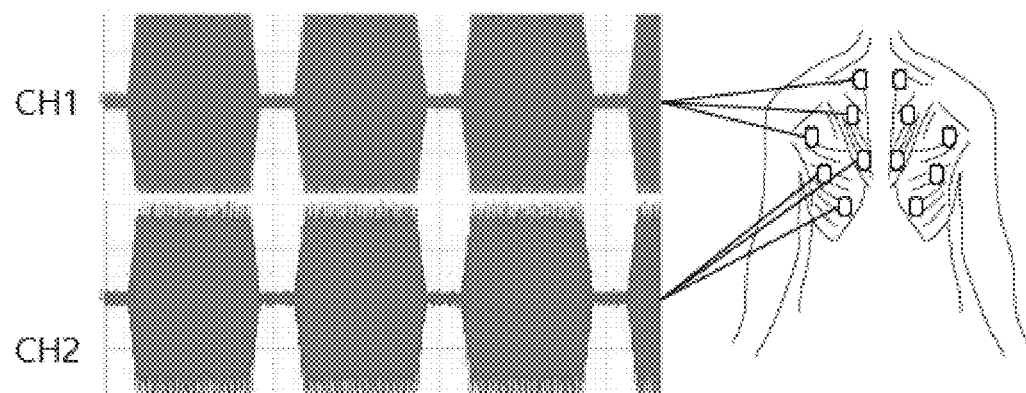
FIG. 25 is a view showing a use state when the second treatment mode is applied to the back.

Referring to FIG. 24, opposite to FIG. 25, biceps are set as main muscles and triceps are set as auxiliary muscles. In this case, RF energy is applied to the main muscles from the second channel and RF energy is applied to the auxiliary muscles from the first channel. That is, RF energy can be switched and applied in the opposite way to the state shown in FIG. 23. When RF energy is applied with strong first power to the biceps that are main muscles, the triceps that are auxiliary muscles contract and resistance is generated, but the arm is finally bent. Accordingly, an effect like lifting a weight using the biceps is generated.

FIG. 25 is a view showing a use state when the second treatment mode is applied to the back.

Referring to FIG. 25, the second treatment mode may be applied to the back muscles in an embodiment. For example, there are latissimus dorsi, Trapezius, infraspinatus, teres minor, and teres major as applicable back muscles. It is possible to simultaneously contract related back muscles by selecting some of the muscles described above and simultaneously applying RF energy to EMS electrode pads attached to skins adjacent to the muscles.

Hereafter, a method of controlling the apparatus of muscle treatment including an EMS electrode according to another embodiment of the present disclosure is described in detail.

Figure 26:
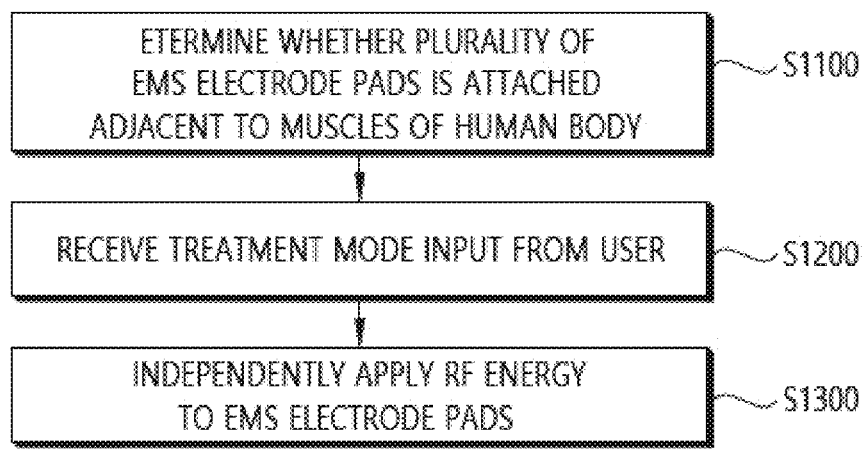
FIG. 26 is a flowchart of a method of controlling the apparatus of muscle treatment including an EMS electrode according to another embodiment of the present disclosure.

FIG. 26 is a flowchart of a method of controlling the apparatus of muscle treatment including an EMS electrode according to another embodiment of the present disclosure.

Referring to FIG. 26, the method according to an embodiment may include determining whether a plurality of EMD electrode pads are attached adjacent to muscles of a human body (S1100), receiving a treatment mode input by a user (S1200), and independently applying RF energy to the EMS electrode pads in accordance with the treatment mode (S1300).

In the embodiment, the EMS electrode modes may be the EMS electrode modes shown in FIGS. 1 to 12 described above, and the RF energy may be controlled by the apparatus of muscle treatment using an EMS electrode pad shown in FIGS. 16 to 25.

The determining of whether a plurality of EMS electrode pads are attached adjacent to muscles of a human body (S1100) is a step of independently measuring the impedance at the EMS electrode pad ends of the electrodes. The impedance of the contact tissues of the human body and the EMS electrode pads are simultaneously measured, and when it is determined the impedance is in a predetermined range, it is possible to determine that the EMS electrode pads are appropriately in contact with the human body. The predetermined range may be set as a predetermined range through a test.

The receiving of a treatment mode input from a user (S1200) is a step of receiving any one of the first treatment mode to the fifth treatment ode described with reference to FIGS. 17 to 21. A user can select a single treatment mode or a sequence each treatment mode.

The independently applying RF energy to the EMD pads in accordance with the treatment mode (S1300) is a step of independently applying RF energy to the EMS electrode modes in accordance with the treatment mode input by the user.

Figure 27:
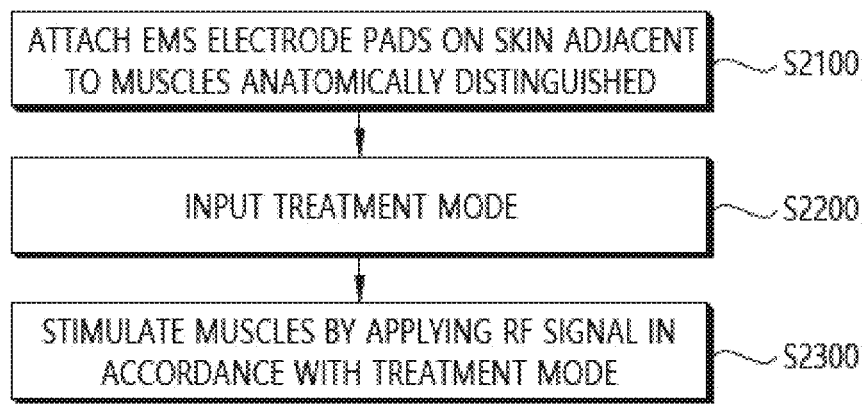
FIG. 27 is a flowchart of a method of muscle treatment using an EMS electrode according to another embodiment of the present disclosure.

FIG. 27 is a flowchart of a method of muscle treatment using an EMS electrode according to another embodiment of the present disclosure.

Referring to FIG. 27, as an embodiment, attaching EMS electrode pads to skins adjacent to muscles that are anatomically distinguished (S2100), receiving a treatment mode (S2200), and stimulating the muscles by applying RF energy in accordance with the treatment mode.

In the attaching EMS electrode pads to skins adjacent to muscles that are anatomically distinguished (S2100), it is possible to select muscles to be treated in accordance with the user, for example, a doctor, and attach EMS electrode pads to the corresponding muscles, respectively.

The inputting of a treatment mode (S2200) is a step of selecting what pattern to use to treat the muscles related to each other by contracting the muscles in accordance with selection of the user to the EMS apparatus. The user can configure a sequence by selecting any one of the first treatment mode to the fifth treatment ode described with reference to FIGS. 17 to 21 or selecting the first treatment mode to the fifth treatment mode.

The stimulating of muscles by applying RF energy in accordance with the treatment mode (S2300) is a step of treating the muscles by applying EF energy to the EMS electrode pads in accordance with the treatment mode or the sequence input by the user.

Thereafter, treatment is finished by removing the EMS electrode pads from the skins.

As described above, an apparatus of muscle treatment including an EMS electrode, a method of controlling the apparatus of muscle treatment including an EMS electrode, and method of muscle treatment using the apparatus of muscle treatment including an EMS electrode can generate a motion similar to a motion that can be actually intentionally generated in accordance with a treatment mode by a user, whereby there is an effect that it is possible to strengthen specific muscles and strengthen and treat related muscles.

The EMS electrode pad according to the present disclosure and the method of electrical muscle stimulation including the EMS electrode pad can minimize the edge effect due to the shape of an electrode for applying electrical energy. Further, since muscles are treated in accordance with an application pattern of RF energy enabling composite motions of a human body, thereby being able to increase the treatment effect.

What is claimed is:

1. An electrical muscle stimulation (EMS) electrode pad comprising:
   a base having a plate-like shape;
   a plurality of electrodes arranged on a lower surface of the base;
   a plurality of first connection portions penetrating the base in a thickness direction and having one side electrically connected with each of the plurality of electrodes; and
   a second connection portion disposed on an upper surface of the base and connected with the other side of the plurality of first connection portions,
   wherein the plurality of electrodes are provided in virtual sections divided by a plurality of first virtual lines and a plurality of second virtual lines on the lower surface of the base, each of the plurality of first virtual lines forms a path directing toward an outer edge portion from a center portion of the lower surface of the base, and each of the plurality of second virtual lines line is configured as an annular path based on which the center portion of the lower surface of the base is an inner side,
   wherein at least some of the plurality of first virtual lines are formed along a curved path,
   wherein at least some of the plurality of first virtual lines are formed along a path of a sinusoidal wave, and
   wherein each of the plurality of electrodes is configured in a shape that fits a shape of a virtual region divided by the first and second virtual lines.

2. The EMS electrode pad of claim 1, wherein the first line has a length smaller than a wavelength of the sinusoidal wave.

3. The EMS electrode pad of claim 1, wherein an interval between one second line and another second line adjacent thereto increases so that a size of the section increases in a direction toward the outer edge portion from the center portion, and at least some of the plurality of electrodes are configured to increase in size in the direction toward the outer edge portion from the center portion.

4. The EMS electrode pad of claim 1, wherein the second line is formed along a stadium-shape path.

5. The EMS electrode pad of claim 1, wherein the plurality of electrodes is insulated from each other on the lower surface of the base.

6. The EMS electrode pad of claim 1, wherein the plurality of electrodes are spaced apart from each other by a predetermined distance on the lower surface of the base.

7. The EMS electrode pad of claim 1, wherein the electrode is formed in a flat plate shape.

8. The EMS electrode pad of claim 1, further comprising:
   a shielding layer configured to cover the second connection portion and formed of an insulating material.

9. The EMS electrode pad of claim 8, further comprising:
   a connector configured to receive RF energy from the outside and electrically connected to one side of the second connection portion.

10. The EMS electrode pad of claim 1, wherein the base is formed of a flexible material.

11. The EMS electrode pad of claim 1, wherein the base is formed of a rigid material.

12. The EMS electrode pad of claim 1 further comprising:
    a dielectric layer covering the plurality of electrodes.

13. The EMS electrode pad of claim 12, wherein, when a lower surface of the dielectric layer comes into contact with a skin, capacitive coupling is formed between the plurality of electrodes in contact with an upper surface of the dielectric layer and the contacted skin.

14. The EMS electrode pad of claim 13, wherein the EMS electrode pad is configured as a pair to receive bipolar RF energy.

15. The EMS electrode pad of claim 13, wherein the dielectric layer is formed of ceramic or polytetrafluoroethylene (PTFE).

16. The EMS electrode pad of claim 1 further comprising:
    a conductive layer provided on a surface of the plurality of electrodes which comes into contact with the skin.

17. The EMS electrode pad of claim 16, wherein the conductive layer is formed of graphene.

18. The EMS electrode pad of claim 16, wherein the conductive layer is provided in each of the plurality of electrodes.

19. The EMS electrode pad of claim 16, wherein the conductive layer is configured to cover the plurality of electrodes.

* * * * *